(12) United States Patent
Ishii et al.

(10) Patent No.: US 7,982,974 B2
(45) Date of Patent: Jul. 19, 2011

(54) IMAGE PICKUP APPARATUS

(75) Inventors: Hiroshi Ishii, Tokyo (JP); Seiji Iwasaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 387 days.

(21) Appl. No.: 12/207,953

(22) Filed: Sep. 10, 2008

(65) Prior Publication Data

US 2009/0010140 A1  Jan. 8, 2009

Related U.S. Application Data

(63) Continuation of application No. PCT/JP2007/052644, filed on Feb. 14, 2007.

(30) Foreign Application Priority Data

Mar. 15, 2006 (JP) ................. 2006-071656

(51) Int. Cl.
*G02B 5/00* (2006.01)
*G02B 15/00* (2006.01)

(52) U.S. Cl. .................... 359/739; 359/676

(58) Field of Classification Search .......... 359/676–698, 359/738–740
See application file for complete search history.

(56) References Cited

U.S. PATENT DOCUMENTS

| 3,883,228 | A | * | 5/1975 | Betensky | 359/679 |
|---|---|---|---|---|---|
| 4,445,764 | A | * | 5/1984 | Matsumura | 396/273 |
| 5,970,260 | A | | 10/1999 | Nakayama et al. | |
| 7,635,229 | B2 | * | 12/2009 | Yasunaga | 396/508 |
| 2005/0159642 | A1 | | 7/2005 | Kawano et al. | |

FOREIGN PATENT DOCUMENTS

| JP | 63-078119 | | 4/1988 |
|---|---|---|---|
| JP | 04-212135 | | 8/1992 |
| JP | 07-140401 | | 6/1995 |
| JP | 07-264886 | | 10/1995 |
| JP | 09-318987 | | 12/1997 |
| JP | 09-322566 | | 12/1997 |
| JP | 10-033462 | | 2/1998 |
| JP | 2004-248877 | | 9/2004 |
| JP | 2005-111245 | | 4/2005 |
| JP | 2007003815 A | * | 1/2007 |
| WO | WO 2004/074354 A1 | | 9/2004 |

OTHER PUBLICATIONS

Extended Supplementary European Search Report dated Mar. 9, 2010.

* cited by examiner

*Primary Examiner* — Darryl J Collins
(74) *Attorney, Agent, or Firm* — Scully, Scott, Murphy & Presser, P.C.

(57) ABSTRACT

An image pickup apparatus having a lens unit configured to include a plurality of lenses and a variable aperture mechanism capable of varying an aperture opening diameter, the image pickup apparatus including: in the lens unit, a variable aperture unit configured by integrating the variable aperture mechanism and the single lenses of the lens unit using a fixing portion.

14 Claims, 14 Drawing Sheets

IMAGE PICKUP APPARATUS

CROSS REFERENCE TO RELATED APPLICATION

This application is a continuation application of PCT/JP2007/052644 filed on Feb. 14, 2007 and claims benefit of Japanese Application No. 2006-071656 filed in Japan on Mar. 15, 2006, the contents of which are incorporated herein by this reference.

BACKGROUND OF INVENTION

1. Field of the Invention

The present invention relates to a small-size image pickup apparatus, and specifically to an image pickup apparatus for an endoscope including an image pickup unit having a variable aperture mechanism for lenses in an objective optical system of the endoscope.

2. Description of the Related Art

Endoscopes have been widely used in the medical and other fields for some time. By inserting an elongated insertion portion or the like into a body cavity, it is possible to observe organs in the body cavity. Where necessary, various treatments can be performed by inserting treatment instruments into a treatment instrument passing channel. Endoscopes include a bending portion at a distal end side of the insertion portion, and it is possible to change an observation direction by performing operations on an operation portion.

Image pickup apparatus used in the above-described endoscope, super minisize cameras and the like have a lens configuration with a single focal distance, so-called fixed focal point lenses, due to the requirements of miniaturization. When a variable aperture is included, however, it is possible to move the focal distance towards a nearer side by reducing the size of the opening of the variable aperture.

Japanese Patent Application Laid-Open Publication No. 9-318987 discloses technology relating to an image pickup apparatus which includes a lens portion formed to have a fixed focal point, a variable aperture having a rotation member for restricting light from the lens portion, and a driving unit for driving in forwards and backwards directions with respect to the lens portion. The arrangement is such that as the rotation member is rotated by the driving unit, the lens portion is caused to move backwards and forwards.

In conventional image pickup apparatus, because a position of the focal point changed by using a variable aperture, it is difficult to secure suitable optical characteristics. To deal with this fault, the image pickup apparatus may be provided with a bifocal lens (or multiple focal lens) having the suitable optical characteristics. Alternatively, a lens can be moved to match a focal point position as in the image pickup apparatus as disclosed in Japanese Patent Application Laid-Open Publication No. 9-318987.

However, in the image pickup apparatus recorded in Japanese Patent Application Laid-Open Publication No. 9-318987, a driving unit for moving the lens is required.

Moreover, the variable aperture mechanism which forms the variable aperture has a complex structure made up of members with a low degree of strength. Consequently, to obtain suitable optical characteristics with a variable aperture mechanism installed in an image pickup unit including a bifocal lens, it is necessary to position the variable aperture mechanism with precision in relation to the bifocal lens.

SUMMARY OF THE INVENTION

The image pickup apparatus of the present invention is an image pickup apparatus having a lens unit configured to include a plurality of lenses and a variable aperture mechanism operable to vary an aperture opening diameter, the image pickup apparatus includes in the lens unit a variable aperture unit configured by integrating the variable aperture mechanism and one of the plurality of lenses of the lens unit using a fixing portion.

DETAILED DESCRIPTION OF THE PREFERRED EMBODIMENT(S)

The following describes embodiments of the present invention with reference to the drawings.

First Embodiment

An image pickup apparatus of a first embodiment of the present invention is described with reference to FIG. 1 to FIG. 9. Note that the present embodiment describes an example of a configuration in which the image pickup apparatus of the present invention is used in an endoscope. However, the image pickup apparatus of the present invention is not limited to being used in an endoscope but can be applied in other imaging equipment such small-size cameras.

Figure 1:
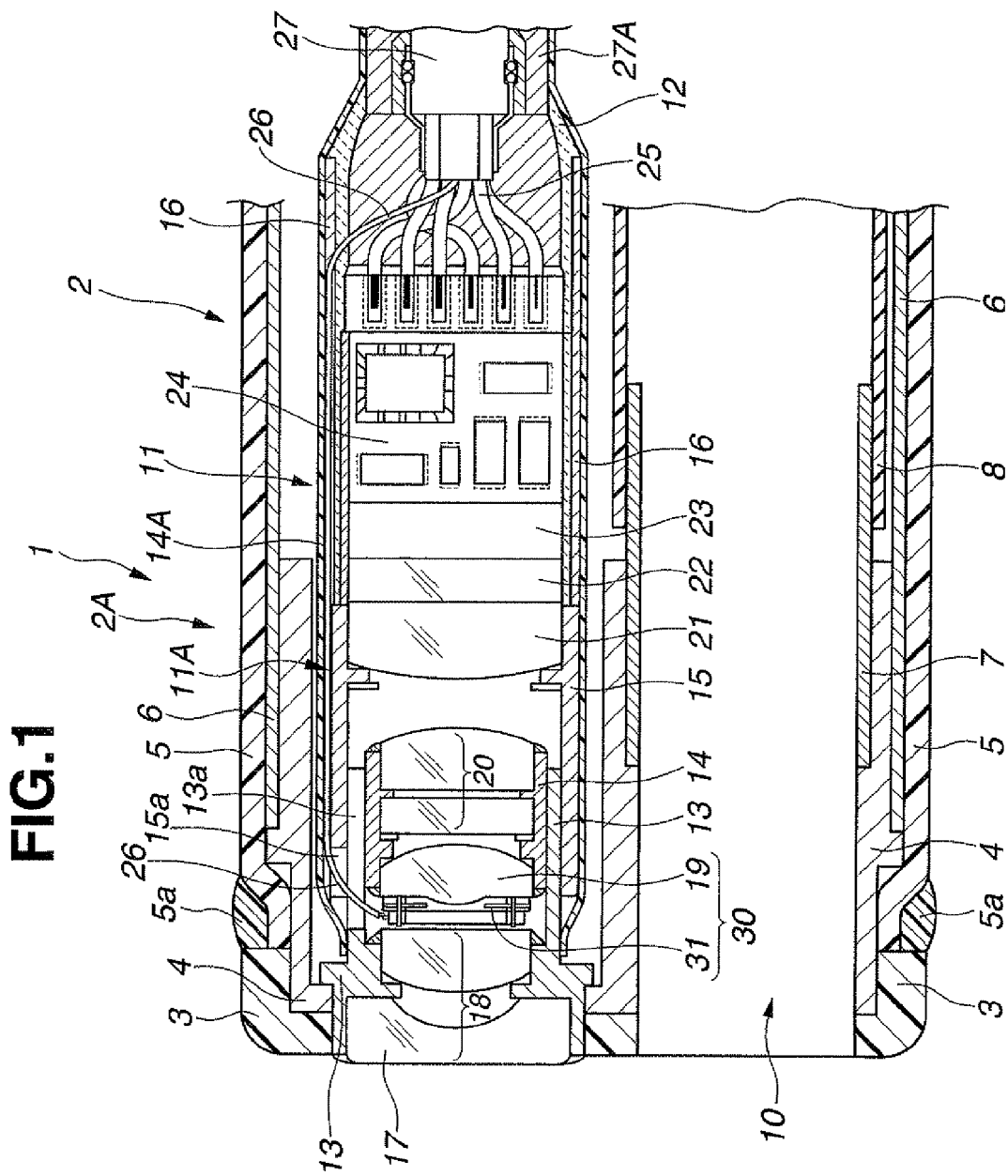
FIG. 1 is a cross-sectional view showing an image pickup apparatus of a first embodiment of the present invention to describe a configuration of a distal end side of an endoscope insertion portion equipped with the image pickup apparatus.

As shown in FIG. 1, an image pickup apparatus 1, which is an image pickup means, is provided in a rigid distal end portion 2A which forms an endoscope insertion portion (hereinafter referred to as "insertion portion") 2 of an endoscope or the like.

When the endoscope is in use, the image pickup apparatus is connected to external devices not shown such as a video processor, a light source apparatus and a monitor, to form an endoscope system. The endoscope includes an elongated flexible insertion portion 2, an operation portion (not shown) connected to the proximal end side of the insertion portion 2, and a universal cord not shown which extends from an operation portion side (not shown). Through the universal cord are passed parts such as a signal cable 27 extending from the image pickup apparatus 1 provided in the distal end portion 2A and light-guiding fibers not shown in the drawing which transmit illumination light from a light source apparatus. At an end thereof, the universal cord is equipped with a connector portion not shown which is detachably connected to the light source apparatus and the video processor.

In order of appearance from the distal end side, the insertion portion 2 includes a rigid distal end portion 2A, a bending portion not shown which is bendable and connected to a proximal end of the distal end portion 2A, and an elongated flexible tube not shown connected to the proximal end of the bending portion.

Light-guiding fibers are passed through the insertion portion 2 to transmit illumination light. The light-guiding fibers are passed through the universal cord via the operation portion. A proximal end of the light-guiding fibers is connected to a light-guiding connector not shown of the light source apparatus.

A distal end section of the light-guiding fibers is fixed within the distal end portion 2A. An illumination window, not shown, of an illumination unit which is an illumination optical system is provided in a distal end section of the distal end portion 2A, and illuminating light transmitted by the light-guiding fibers is emitted to an external portion via the illumination window. A distal end cover 3 is provided on a distal end surface of the distal end portion 2A.

A treatment instrument channel (also called a forceps channel) 10 which is a tubular path capable of passing treatment instruments, such as forceps for surgical use, is provided in the insertion portion 2. The distal end of the treatment instrument channel 10 is open in the distal end surface of the distal end cover 3. The treatment instrument channel can also be used as a suction channel.

The treatment instrument channel 10 branches at the proximal end side of the insertion portion 2 with one branch communicated with a treatment instrument insertion opening, not shown, which is provided in the operation portion. The other of the branches passes through the insertion portion 2 and the universal cord. A proximal end of the same branch is connected to a suction unit via a connector portion not shown. Hence, it is possible to introduce treatment instruments into a body cavity via the treatment instrument channel 10 and to suck out bodily fluids and the like from the body cavity.

The distal end surface of the distal end cover 3 is provided with an air/water nozzle not shown. The air/water nozzle emits, in an air supplying or a water supplying, a jet of cleaning liquid or gas towards a distal end lens 17 which forms an observation window of a later-described observation optical system.

The following describes a specific configuration of the distal end portion 2A which includes the image pickup apparatus 1.

As shown in FIG. 1, an image pickup unit 11 which configures the image pickup apparatus 1 is provided in the distal end portion 2A. Note that a specific configuration of the image pickup unit 11 is described in a later section.

A distal end cover 3 is provided at the distal end side of the distal end portion 2A. The distal end cover 3 is formed using a resin member or the like and is provided so as to cover a distal end side of a cylindrical member 4 in which a plurality of hole portions are formed. A ring-like distal-end bending piece 6 which configures the farthest tip of the bending portion is fixed to the proximal end side of the cylindrical member 4.

A skin 5 is provided to cover the cylindrical member 4 and the distal-end bending piece 6 on the external circumference thereof. A distal end side of the skin 5 is attached to the distal end portion 2A by a bonding portion 5a.

Among the plurality of hole portions formed in the cylindrical member 4, one forms a distal end section of the treatment instrument channel 10, and another is an image pickup apparatus hole portion which houses the image pickup unit 11, as shown in FIG. 1. Note that other hole portions not shown contain the illumination unit and the air/water nozzle.

Illumination units may, for instance, be insertably installed in two of the hole portions. At proximal end sections of the illumination units are arranged distal end sections of the light-guiding fibers respectively. Note that an illumination lens which forms an illumination window is provided at the distal end of each illumination unit.

A first lens frame 13 in which is fixed the distal end lens 17 or the like as the observation window of the image pickup unit 11, is insertably fitted into the hole portion for housing the image pickup apparatus. The distal end surface of the distal end lens 17 is provided so as to be exposed at the distal end surface of the distal end portion 2A.

The image pickup unit 11 of the present embodiment is configured to include a lens unit 11A having a variable aperture unit 30 described in a later section, an image pickup device 23 such as a CCD (Charge Coupled Device), a CMOS (Complementary Metal-Oxide Semiconductor), and a circuit substrate 24.

The lens unit 11A is configured to include a first lens group 1S, a second lens group 19, a third lens group 20, a fourth lens group 21, a first lens frame 13, a third lens frame 14, a fourth lens frame 15, and a variable aperture unit 30, as shown in FIG. 1. Specifically, the variable aperture unit 30 is configured to include the second lens 19 and a variable aperture mechanism 31.

In the present embodiment, the first tens group 18, which may have two objective lenses including the distal end lens 17, is held by the first lens frame 13.

The second lens, which is a bifocal lens 19, being fixed to the variable aperture mechanism 31, is held at a distal end side of the third lens frame 14. Thus, the variable aperture unit 30 which includes the bifocal lens 19 is fixed to the third lens frame 14 as a result of the bifocal lens 19 being held by the third lens frame 14.

At the proximal end side, on the other hand, the third lens frame 14 holds the third lens group 20, which may include two lenses. The fourth lens frame 15 holds the fourth lens 21 which may be a single objective lens.

Note that a specific configuration of the variable aperture unit 30 is described in a later section.

A cover glass 22 provided in parallel with the proximal end side of the fourth lens held at the deepest proximal end of the fourth lens frame 15, is provided on a light-receiving surface side of the image pickup device 23. The image pickup device 23 is connected to the circuit substrate 24. The circuit substrate 24 includes electric parts and a wiring pattern, generates an image signal corresponding to an optical image formed on the light-receiving surface of the image pickup device 23, and outputs the resulting image signal to the signal cable 27. Note that the circuit substrate 24 is connected to a plurality of signal lines 25 included in the signal cables 27 by soldering or the like.

The cover glass 22, the image pickup device 23, an external circumferential portion of the circuit substrate 24, and a distal end section of the signal cables 27 are covered integrally by a sealing portion 12 which is an insulator sealing resin or the like, and further covered by a reinforcing ring portion 16 and an insulating tube 14A. The insulating tube 14A is provided from the proximal end side of the first lens frame 13 at the distal end portion of the image pickup unit 11 all along an entire length of a connecting tube 27A which passes the signal cable 27, covering the fourth lens frame 15, the reinforcing ring portion 16, and the like.

The signal cable 27 transmits the image signal acquired by the image pickup unit 11 to a signal processing circuit in the video processor.

The signal cable 27 includes a signal line 26 for controlling the variable aperture mechanism 31 of the variable aperture unit 30. The signal line 26 is provided inside the image pickup unit 11 as shown in FIG. 1. A distal end portion of the signal line 26 is electrically connected to the variable aperture mechanism 31 of the variable aperture unit 30. On the other hand, a proximal end portion of the signal line 26 is electrically connected to a driving control circuit in the video processor in a similar manner to the signal cable 27.

In the image pickup unit 11 of the present embodiment the variable aperture unit 30 including the bifocal lens 19 is provided between the first lens group 18 and the third lens group 20.

The following describes a specific configuration and manufacturing method of the variable aperture unit 30 with reference to FIGS. 1 to 4.

Figure 2:
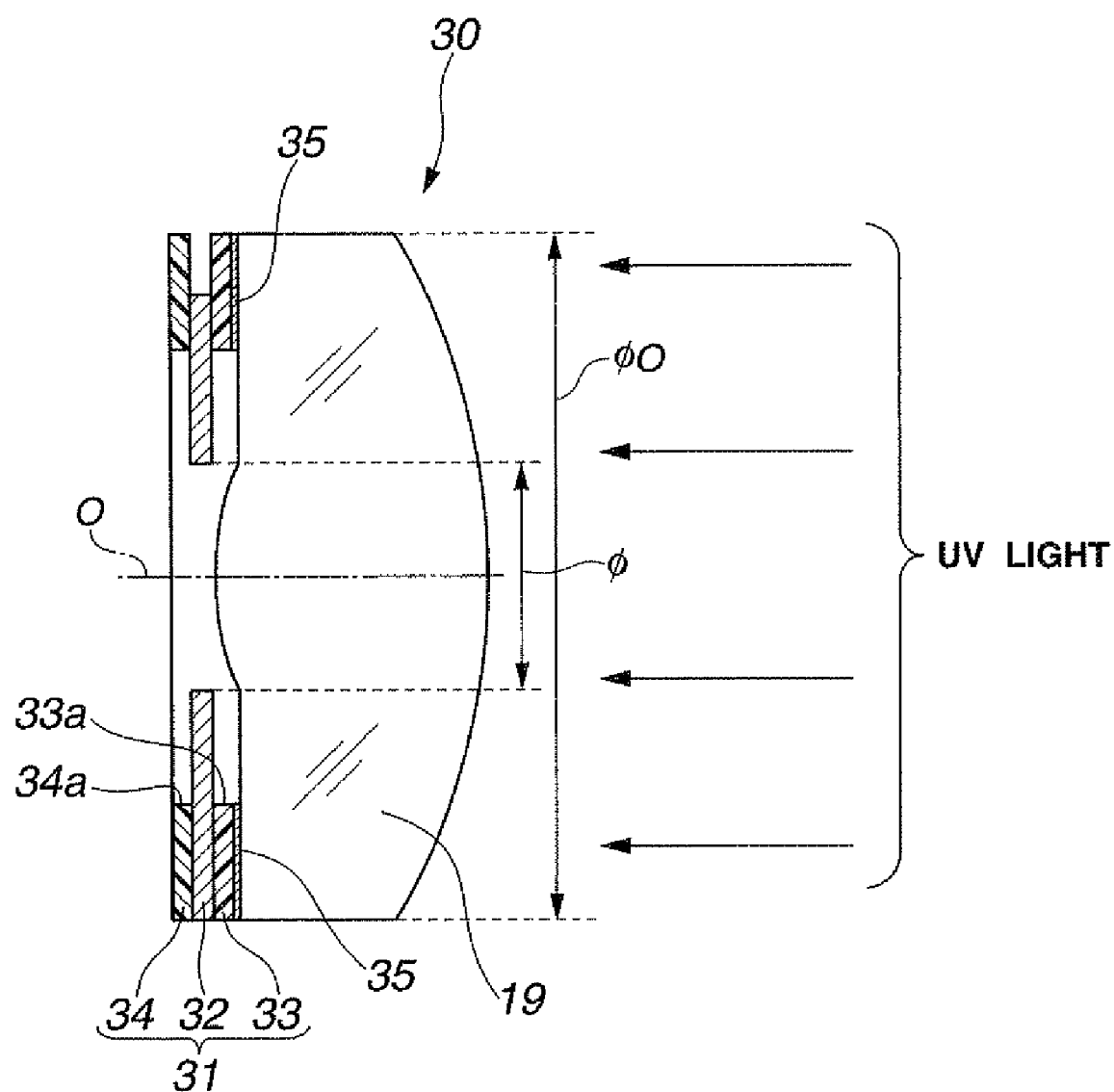
FIG. 2 is a diagram for describing a configuration and a manufacturing method of a variable aperture unit of the image pickup apparatus.

The variable aperture unit 30 is configured to include the bifocal lens 19, which is an objective lens, and the variable aperture mechanism 31 as shown in FIGS. 1 and 2. A fixing portion 35 is provided for fixing the bifocal lens 19 on a drivable surface side of the variable aperture mechanism 31.

Note that the drivable surface side of the variable aperture mechanism 31 refers to surface portion of the variable aperture mechanism 31 at which the bifocal lens 19 is fixed by the fixing portion 35 and still allow the variable aperture mechanism 31 to be driven (i.e. allow the aperture opening diameter to be varied), which is, in the present embodiment, the emission surface side of the variable aperture mechanism 31.

The bifocal lens 19 has characteristics of a multiple lens as shown in FIG. 2. The bifocal lens 19 is configured to include a convex lens section of a diameter corresponding to an aperture internal diameter $\phi$ for a stopped down state of the aperture in the variable aperture mechanism 31. The maximum diameter of the lens is $\phi 0$. Note that although in the present embodiment, the bifocal lens 19 is used as the objective lens in the variable aperture unit 30, the objective lens is not limited to being a bifocal lens. Another type of objective lens may be used.

The variable aperture mechanism 31 is mainly comprised of an aperture blade portion 32, a first substrate 33, and a second substrate 34. The aperture blade portion 32 changes the aperture opening diameter. The fixing portion 35 for fixing the bifocal lens 19 is provided on an emission surface side of the first substrate 33. The aperture blade portion 32 is sandwiched between the first substrate 33 and the second substrate 34.

The fixing portion 35 for fixing the bifocal lens 19 is provided on the emission surface side of the first substrate 33. The fixing portion 35 is, for example, a UV light-cured resin member having a property by which a photopolymerization reaction is started by irradiation with UV light. The bifocal lens 19 is attached in a fixed manner to the first substrate 33 using the UV light-cured resin member having the above-described property. Note that although the UV light-cured resin member is used as the fixing portion 35 in the present embodiment, the fixing portion 35 is not limited to being a UV light-cured resin member, and another connecting member may be used. Where another member is used, it is desirable that the fixing portion 35 is transparent to light.

The following describes the manufacturing method of the variable aperture unit 30 with reference to FIG. 2.

In the present embodiment, the UV light-cured resin member which is to form the fixing portion 35 is applied to the emission surface side of the first substrate 33 in the variable aperture mechanism 31. The bifocal lens 19 is positioned on the fixing portion 35 so that incident surface side of the bifocal lens 19 overlaps the fixing portion 35. The incident surface side of the bifocal lens 19 is then fixed in place by irradiation with UV light.

When positioning the bifocal lens 19, the aperture opening diameter of the aperture blade portion 32 of the variable aperture mechanism 31 is stopped down to a minimum size. In other words the positioning of the bifocal lens 19 with respect to the variable aperture mechanism 31 is determined in a state in which the aperture diameter has been set to an aperture internal diameter $\phi$ shown in FIG. 2 using the aperture blade portion 32.

Note that the positioning of the bifocal lens 19 refers to the centering the bifocal lens 19 by matching a longitudinal central axis O in the aperture opening of the aperture blade portion 32 with a focal point of the bifocal lens 19 (convex lens section).

After centering the bifocal lens 19, the entire region of the emission surface side of the bifocal lens 19 is irradiated with UV light as shown in FIG. 2 by a UV light by a UV irradiation apparatus not shown. The irradiation starts a photopolymerization reaction in the UV light-cured resin member which configures the fixing portion 35, causing the UV light-cured resin member to harden. As a result, the bifocal lens 19 is fixed on the first substrate 33 in a centered state. Thus, the variable aperture unit 30 of the present embodiment can be easily manufactured.

The following describes a specific configuration of the variable aperture mechanism 31 of the variable aperture unit 30 according to the present embodiment with reference to FIGS. 3 to 6.

Figure 3:
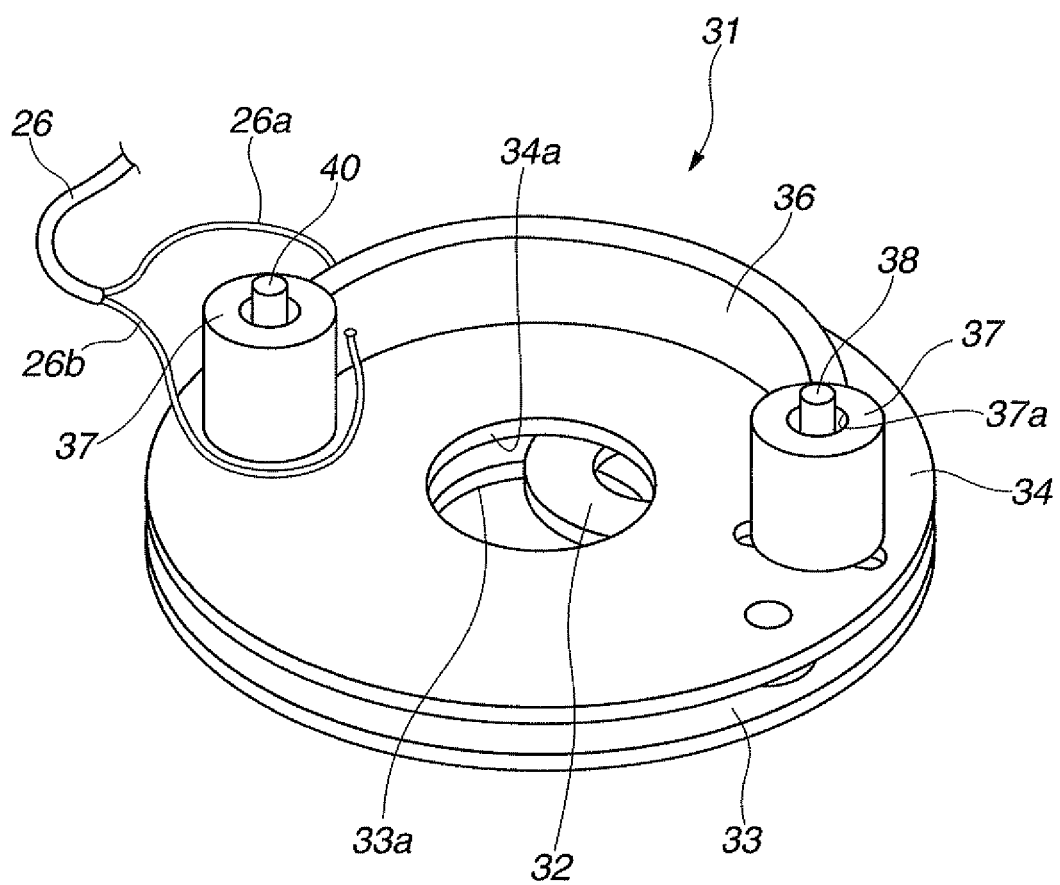
FIG. 3 is a perspective view for describing a variable aperture mechanism.

As shown in FIG. 3, an ion conducting actuator 36 is provided on the second substrate 34 of the variable aperture mechanism 31. The ion conducting actuator 36 has a deformation property described in a later section. Making use of the deformation property, the ion conducting actuator 36 rotates the aperture blade portion 32, which is rotatably installed between the first substrate 33 and the second substrate 34 and thereby changes the aperture opening diameter.

The ion conducting actuator 36 has a property by which positive ions in a polymer electrolyte are moved towards a cathode side by application of a voltage and the resulting difference in swelling between the front and rear of the polymer electrolyte causes deformation. The ion conducting actuator 36 is a plate formed to be substantially arc-like. Cylindrical connecting portions 37 are provided at both ends of the ion conducting actuator 36. The connecting portions 37 include through holes 37a for passing a driving pin 38 and a fixed pin 40 which are described in a later section.

Signal lines 26a and 26b are electrically connected to front and rear surfaces of the ion conducting actuator 36 by soldering or the like. The signal lines 26a and 26b are, for example, bundled together in proximity to one of the connecting portions 37 to form a signal cable 26. The signal cable 26 passes into the signal cable 27 provided in the image pickup unit 11 via cut-out sections 13a and 15a, as shown in FIG. 1.

Connection positions of the two signal lines 26a and 26b with respect to the ion conducting actuator 36 are not limited to the connection positions shown in FIG. 3. Any connection positions which allow the application of a voltage and the resulting deformation to the ion conducting actuator 36 may be used.

Figure 4:
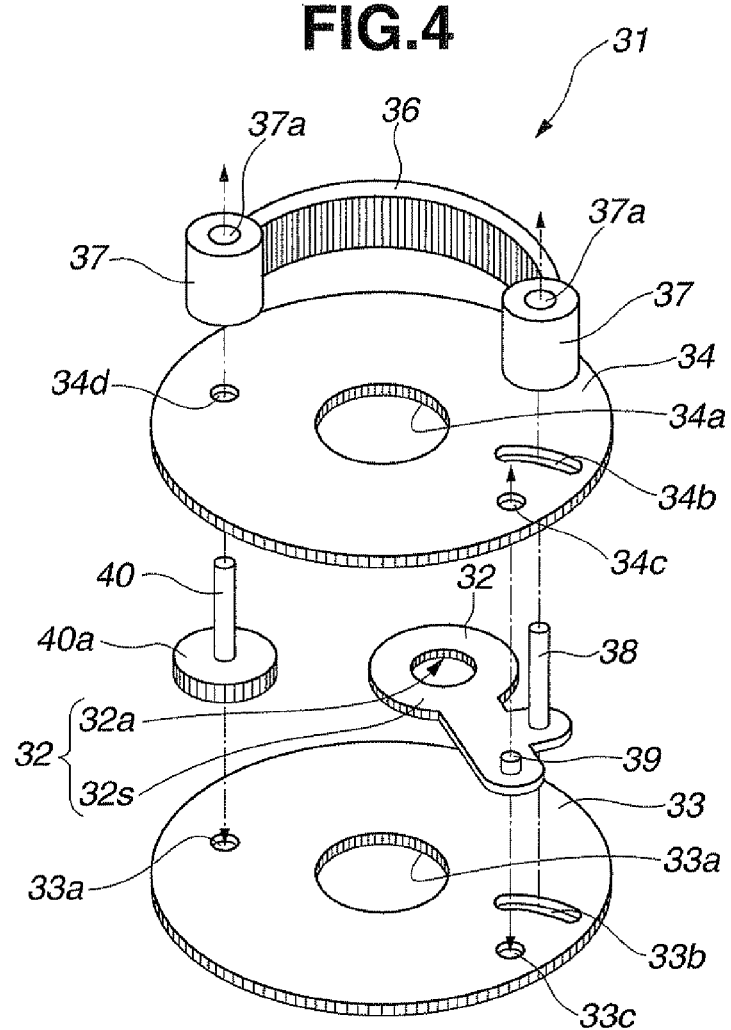
FIG. 4 is an exploded assembly diagram of the variable aperture mechanism.

The following describes an assembly procedure and configuration of the variable aperture mechanism 31 with reference to FIG. 4.

As shown in FIG. 4, the first substrate 33 has formed therein a fixed aperture opening 33a which forms the maximum aperture opening diameter, a slit 33b, a rotation pin hole 33c and a fixed pin hole 33d. The slit 33b is a hole which allows sliding movement of the driving pin 38, and describes a curve extending towards an external circumference from a side of an opening 33a. A rotation pin 39 is provided in the rotation pin hole 33c. A fixed pin 40 is fixed in the fixed pin hole 33d.

The second substrate 34, on the other hand, has formed therein a fixed aperture opening 34a, a slit 34b, a rotation pin hole 34c, and a fixed pin hole 34d resembling those in the first substrate 33. Thus, since the first substrate 33 and the second substrate 34 have the same form, the first substrate 33 and the second substrate 34 can be easily manufactured using a single pressing process.

The aperture blade portion 32, which is rotatably held between the first substrate 33 and the second substrate 34, is configured to include a light-blocking portion 32s having an aperture opening 32a with the smallest aperture opening diameter, the rotation pin 39 and the driving pin 38. The rotation pin 39 is provided at a proximal end side of the body including the aperture opening 32a. The driving pin 38 is provided in proximity to the rotation pin 39. Note that an external diameter of the light-blocking portion 32 is larger than the external diameters of the fixed aperture openings 33a and 34a.

The rotation pin 39 is cylindrical and is provided so as to project from front and rear surfaces of the body of the aperture blade portion 32. The rotation pin 39 is integrated with the front and rear surfaces of the body or provided as a separate entity to the body. The rotation pin 39 projecting on the side of the first substrate 33 is rotatably provided in the rotation pin hole 33c of the first substrate 33. The rotation pin 39 projecting on the side of the second substrate 33 is rotatably provided in the rotation pin hole 34c of the second substrate 34.

The driving pin 38 is cylindrical and is provided so as to project from front and rear surfaces of the body of the aperture blade portion 32. The driving pin 38 is either integrated with the front and rear surfaces of the body or provided as a separate entity to the body. The driving pin 38 projecting on the side of the first substrate 33 passes through the slit 33b in the first substrate 33. The driving pin 38 projecting on the side of the second substrate 34 passes through the slit 34b in the second substrate 34. The driving pin 38 projecting on the side of the second substrate 34 is formed with sufficient length to pass through and engage with the through hole 37a in the connecting portion 37 of the ion conducting actuator 36.

The fixed pin 40 is cylindrical and projects from front and rear surfaces of a disc 40a disposed between the first substrate 33 and the second substrate 34. The fixed pin 40 may be integrated with the disc 40a or provided as a separate entity.

The fixed pin 40 projecting on the side of the first substrate 33 is fitted into the fixed pin hole 33d of the first substrate 33. The fixed pin 40 projecting on the side of the second substrate 34 is passed through the fixed pin hole 34d of the second substrate 34. The fixed pin 38 projecting on the side of the second substrate 34 is formed with sufficient length to pass through and engage with the through hole 37a in the connecting portion 37 of the ion conducting actuator 36.

In a procedure to assemble the variable aperture mechanism 31 of the above described configuration, a worker may for instance locate the rotation pin 39 in the rotation pin hole 33c of the first substrate 33 and then simultaneously fit the fixed pin 40 into the fixed pin hole 33d and pass the driving pin 38 of the aperture blade portion 32 through the slit 33b of the first substrate 33, as shown in FIG. 4.

Next, with the assembly in the above-described state, the worker simultaneously passes the fixed pin 40 through the fixed pin hole 34d of the second substrate 34, locates the rotation pin 39 of the aperture blade portion 32 in the rotation pin hole 34c of the second substrate 34 and passes the driving pin 38 through the slit 34b of the second substrate 34.

The worker then fits the fixed pin 40 protruding from the fixed pin hole 34d of the second substrate 34 and the driving pin 38 protruding from the slit 34b into the through holes 37a of the two connecting portions 37 of the ion conducting actuator 36.

Thereafter, the worker electrically connects the signal lines 26a and 26b of the signal cable 26 to the front and rear surfaces of the ion conducting actuator 36 by soldering or the like. Note that the signal lines 26a and 26b may be connected in advance to the ion conducting actuator 36.

According to the above-described assembly procedure, it is possible to manufacture the variable aperture mechanism 31 of the present embodiment by simple assembly.

The following describes operations of the image pickup apparatus 1 of the present embodiment with reference to FIGS. 5 to 9.

The aperture opening diameter of the image pickup apparatus 1 of the present embodiment is changed by a deformation operation of the ion conducting actuator 36 which forms the variable aperture mechanism 31 of the variable aperture unit 30. The deformation operation is realized by changing a driving signal current via the signal cable 26 which is electrically connected to the ion conducting actuator 36.

Note that the current changing operation is actually performed by, for example, a surgeon operating a switch provided on the operation portion not shown of the endoscope. Based on an operation signal outputted from the switch, the driving control circuit located not shown in the video processor is controlled so that the current of the driving signal changes.

Figure 7:
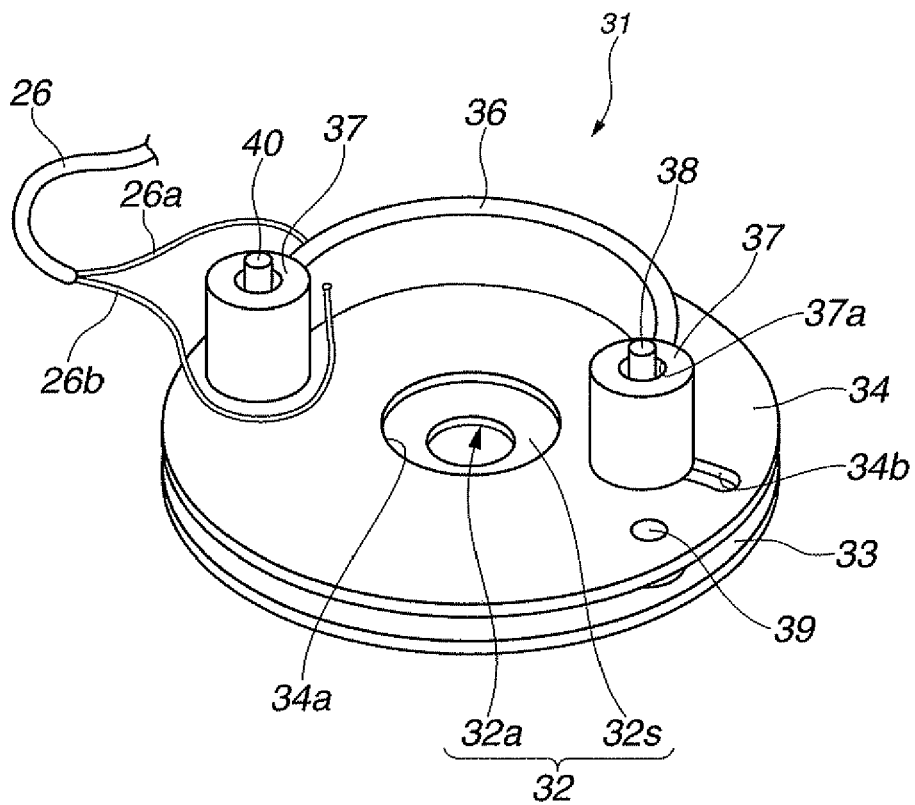
FIG. 7 is an explanatory diagram showing the variable aperture mechanism in a state in which the aperture blade portion is positioned over the fixed aperture opening.

For example, the surgeon may perform an operation on the switch of the operation portion not shown, causing the operation portion to output a driving signal which causes an operation to stop down the aperture of the variable aperture unit 30. A driving signal then flows to the ion conducting actuator 36 configuring the variable aperture mechanism 31 of the variable aperture unit 30 via the signal lines 26a and 26b. Consequently, a voltage is applied to the ion conducting actuator 36. With the application of the voltage, the ion conducting actuator 36 undergoes a contractile deformation so that the two connecting portions 37 approach each other by moving inward along an arc, as shown in FIG. 7 for instance.

Figure 5:
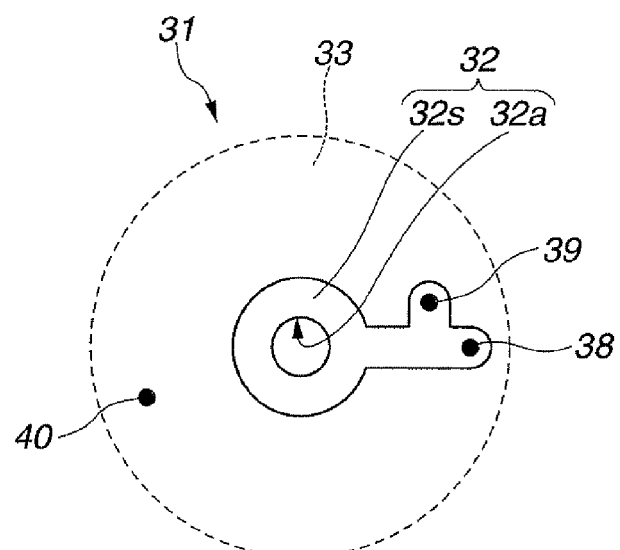
FIG. 5 is a diagram for describing an aperture operation of the variable aperture mechanism and shows a state in which an aperture blade portion is positioned over a fixed aperture opening.

Note that since the ion conducting actuator 36 has one of the connecting portions 37 fixed to the fixed pin 40, it is the other of the connecting portion 37 which moves towards the fixed aperture opening 34a in the deformation operation. The driving pin 38 passing through the other of the connecting portion 37 then moves in the slits 34b and 33b towards the fixed aperture opening 34a, thereby moving the aperture blade portion 32 so that the aperture opening 32a is positioned in the fixed aperture opening 33a of the first substrate 33 and the fixed aperture opening 34a of the second substrate 34, as shown in FIG. 5 and FIG. 7.

Positioning the aperture opening 32a of the aperture blade portion 32 at the center of fixed aperture openings 34a and 33a blocks the fixed aperture openings 34a and 33a with the light-blocking portion 32s. The aperture opening diameter of the variable aperture mechanism 31 is then in a state of being stopped down to a smallest size. In other words, the aperture diameter is the aperture internal diameter 4 shown in FIG. 2 as a result of the positioning of the aperture blade portion 32.

The surgeon may then perform an operation on the operation portion switch not shown to halt the output of the driving signal to the variable aperture unit 30. As a result, the application of the voltage to the ion conducting actuator 36 is halted, causing the connecting portion 37 to move toward the external circumference of the first substrate 33 and the second substrate 34 as shown in FIG. 9 and returning the contracted ion conducting actuator 36 to an original state.

Note that since in the ion conducting actuator 36, one of the connecting portions 37 is fixed to the fixed pin 40, it is the other of the connecting portions 37 which moves towards the external circumference of the substrates 33 and 34 in the deformation operation.

Figure 6:
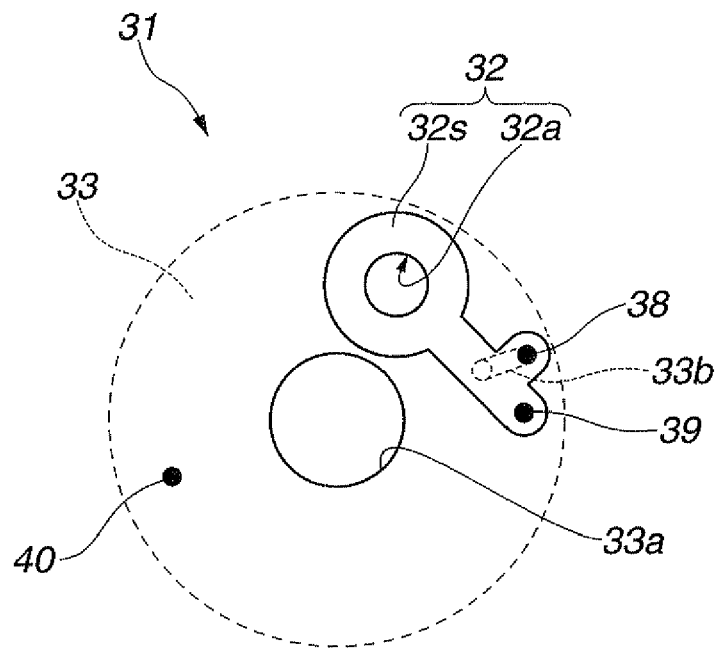
FIG. 6 is a diagram for explaining an aperture operation of the variable aperture mechanism and shows a state in which the aperture blade portion is positioned away from the fixed aperture opening.
Figure 8:
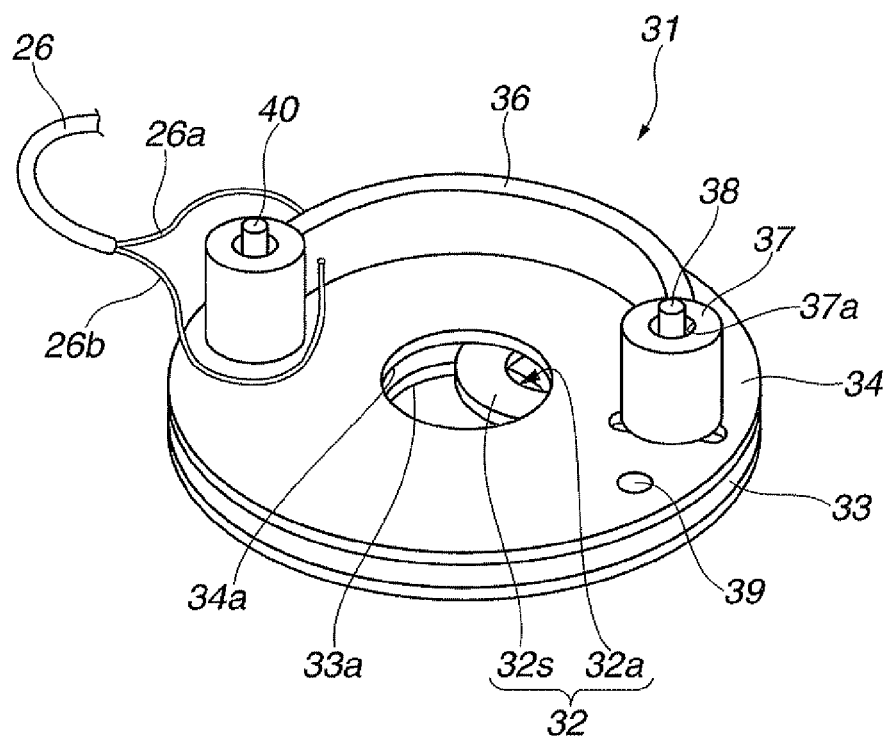
FIG. 8 is an explanatory diagram showing the variable aperture mechanism in an intermediate state in which the aperture blade portion is moving from a stopped down state to an open state.
Figure 9:
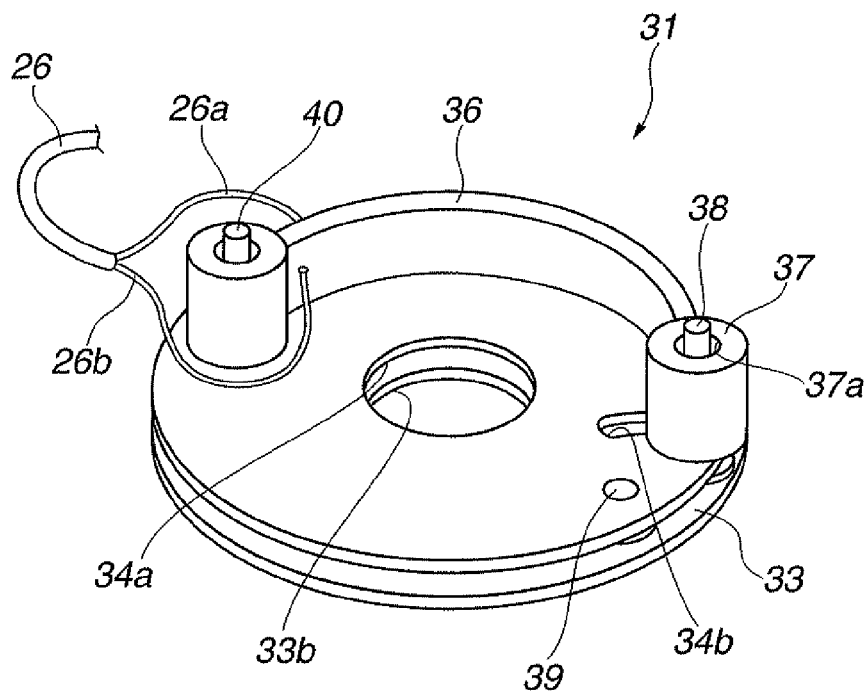
FIG. 9 is an explanatory diagram showing the variable aperture mechanism in a state in which the aperture blade portion is positioned away from the fixed aperture opening.

Thus, the driving pin 38 passing through the other of the connecting portion 37 moves in the slits 34b and 33b in an opposite direction to the movement at aperture stopping down, thereby moving the aperture blade portion 32, via a movement state shown in FIG. 8, to a position away from the fixed aperture openings 34a and 33a of the substrates 33 and 34 as shown in FIG. 6 and FIG. 9.

The fixed aperture openings 34a and 33a are then fully opened to give the maximum aperture opening diameter.

Thus, the first embodiment makes it possible to secure the necessary strength at assembly and when driving the aperture mechanism, and also to obtain a small-size variable aperture unit 30 which can be assembled precisely and efficiently.

Also, the variable aperture unit 30 is fixed using the fixing portion 35 after positioning the bifocal lens 19 and the variable aperture mechanism 31 by centering the bifocal lens 19 when the aperture opening is being stopped down using the aperture blade portion 32. As a result, variation in the aperture internal diameter in the stopped down state can be suppressed. Hence, use of the variable aperture unit 30 makes it possible to realize the image pickup apparatus 1 with favorable optical characteristics.

Moreover, use of the miniaturized variable aperture unit 30 contributes to the miniaturization of the image pickup apparatus 1.

Note that in the first embodiment the variable aperture mechanism 31 which configures the variable aperture unit 30 has a configuration in which the bifocal lens 19 is fixed by lamination via the fixing portion 35 to s planar member formed by the first substrate 33, the second substrate 34 and the like. However, the variable aperture mechanism is not limited to this configuration. For example, the aperture blade portion 32 and the substrates 33 and 34 may be three-dimensionally configured in a way that allows rotation of the aperture blade portion 32. In a variable aperture mechanism of such a configuration, the bifocal lens 19 may be fixed by lamination using the fixing portion 35 in the same way as in the first embodiment.

In the first embodiment, the bifocal lens 19 of the variable aperture unit 30 is provided on the emission surface side of the variable aperture mechanism 31. However, a variable aperture configuration in which the bifocal lens 19 is, for example, provided on the incident surface side of the variable aperture mechanism 31 may be used. When this configuration is used, it may be necessary to move or include other objective lenses or the like for optical reasons.

The following describes a second embodiment of the variable aperture unit 30 with reference to FIG. 10 to FIG. 13.

Second Embodiment

FIG. 10 to FIG. 13 describe the second embodiment. Note that in FIG. 10 to FIG. 13, configuration elements resembling those of the first embodiment are marked with the same reference symbols, and descriptions of these configuration elements have been emitted. Only configuration elements which differ from those of the first embodiment are described.

In the variable aperture unit 30 of the first embodiment, two aperture execution modes, corresponding to the stopped down state and fully open state of the fixed aperture openings 33a and 34a, can be executed by rotating the aperture blade portion 32. However, it is not possible to drop down the fixed aperture openings 33a and 34a in a gradual manner. The variable aperture mechanism 31A of the variable aperture unit 30 of the second embodiment has a configuration which allows fixed aperture openings 33a, 34a and 41a to be gradually stopped down and gradually opened.

Figure 10:
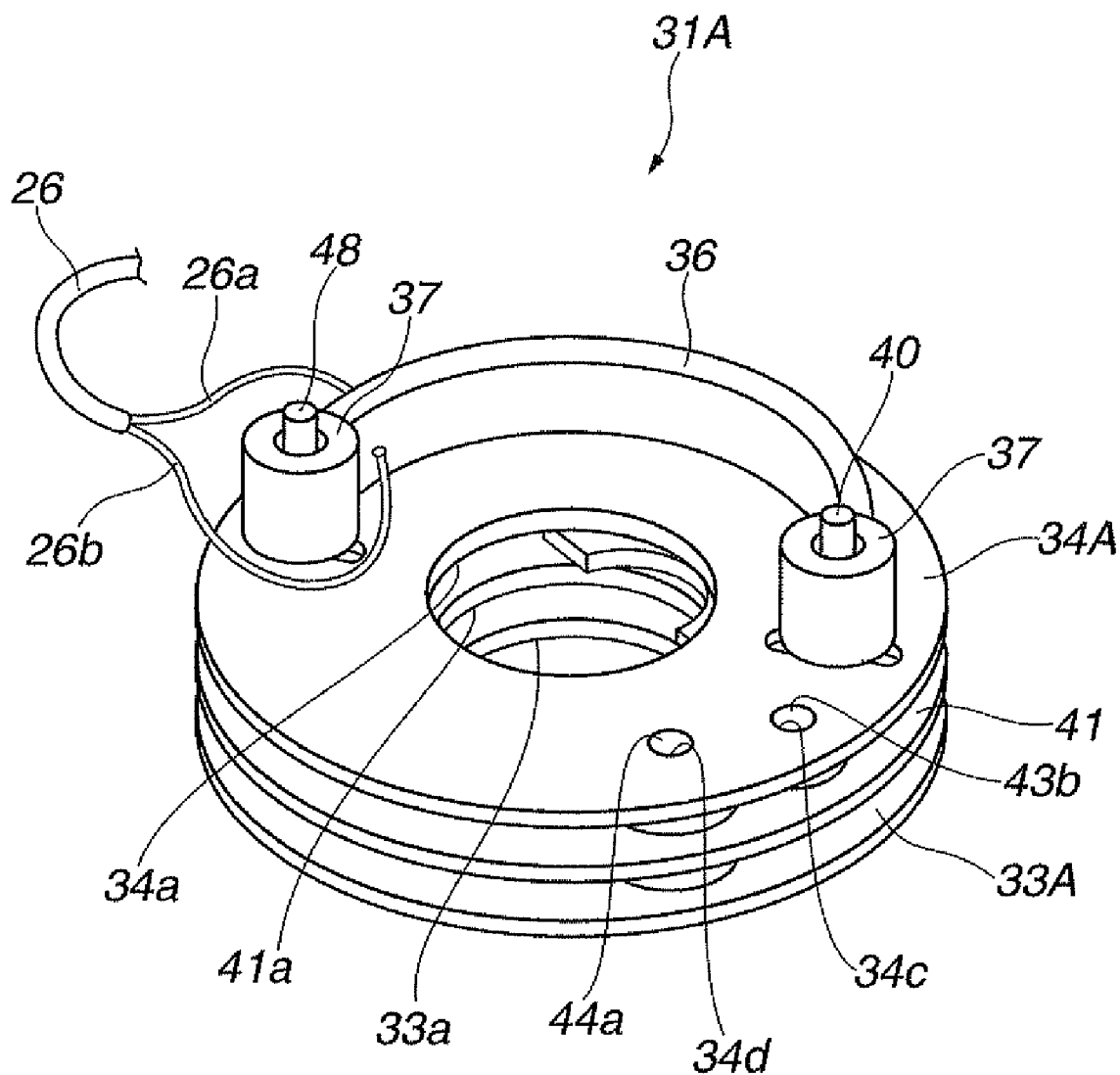
FIG. 10 is a perspective view showing a variable aperture mechanism included in an image pickup apparatus of a second embodiment.

Specifically, the variable aperture unit 30 of the second embodiment includes the variable aperture mechanism 31A shown in FIG. 10. The variable aperture mechanism 31A is configured to include the ion conducting actuator 36, a first substrate 33A, a second substrate 34A, a third substrate 41, a first aperture blade portion 42 and a second aperture blade portion 43, as shown in FIG. 10 to FIG. 13.

Thus, the variable aperture mechanism 31A of the present embodiment is configured to include two blades which form a pair of aperture blade portions. The first aperture blade portion 42 and the second aperture blade portion 43 are provided to allow the fixed aperture openings 33a, 34a and 41a to be stopped down or opened in a gradual manner. Note that the configuration of the fixing portion 35 of the bifocal lens 19 and the first substrate 33A is substantially the same as the corresponding configuration in the first embodiment.

Figure 11:
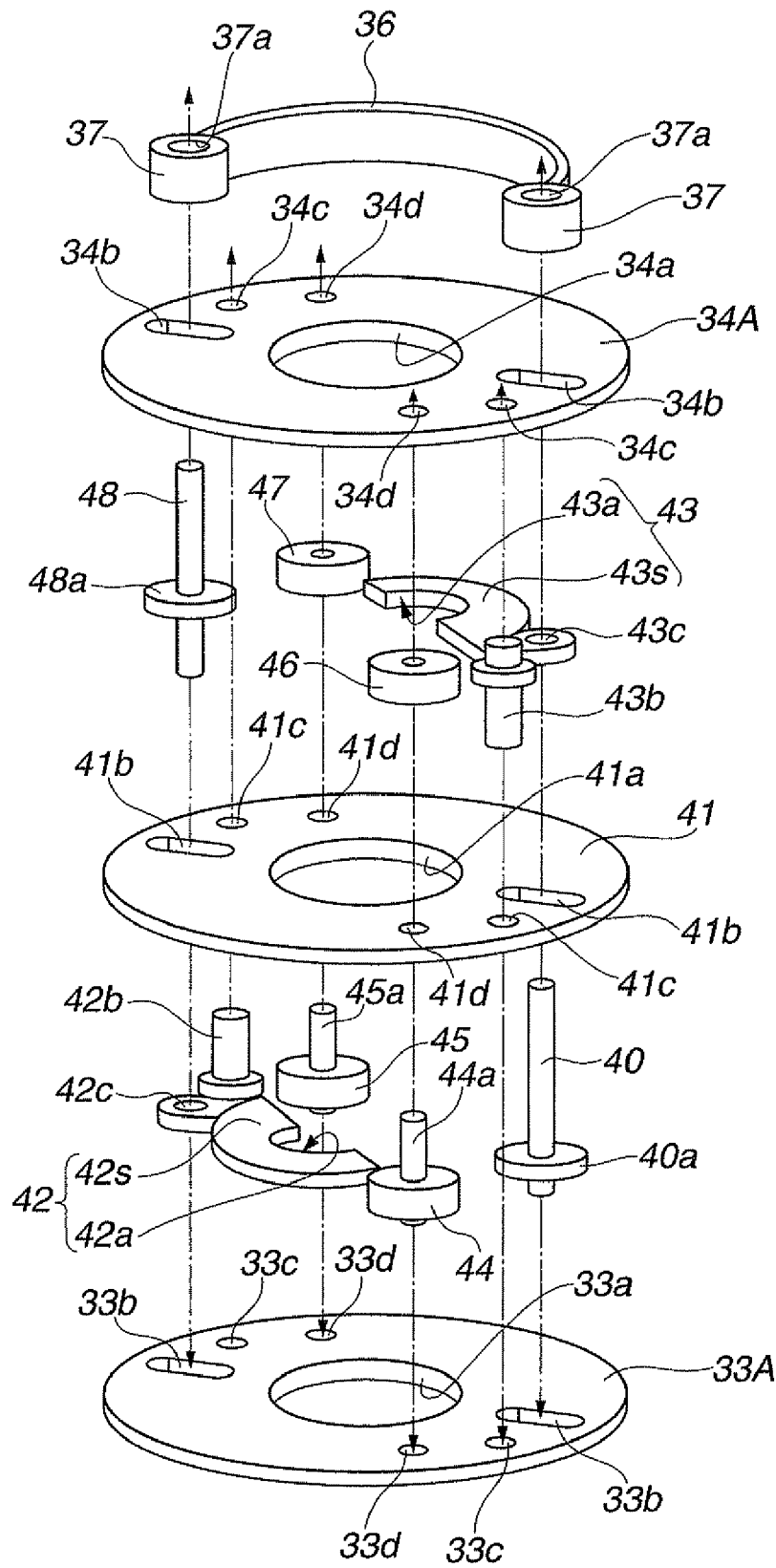
FIG. 11 is an exploded assembly diagram of the variable aperture mechanism of FIG. 10.

The following describes an assembly procedure and configuration of the variable aperture mechanism 31A with reference to FIG. 11.

As shown in FIG. 11, in addition to the configuration elements of the above-described first embodiment, the variable aperture mechanism 31A includes the third substrate 41, the first aperture blade portion 42 and the second aperture blade portion 43 for forming a two-bladed mechanism, a first spacer 44 and a second spacer 45, a first spacer-receiving portion 46 and a second spacer-receiving portion 47, and a first driving pin 40 and a second driving pin 48.

Moreover, a slit 33b, a rotation pin hole 33c and a fixed pin hole 33d are additionally provided in the first substrate 33A, and a slit 34b, a rotation pin hole 34c, and a fixed pin hole 34d are additionally provided in the second substrate 34A. Thus, the first substrate 33A includes the fixed aperture opening 33a, two slits 33b, two rotation pin holes 33c and two fixed pin holes 33d, and the second substrate 34A includes the fixed aperture opening 34a, two slits 34b, two rotation pin holes 34c, and two fixed pin holes 34d. The third substrate 41 also includes the fixed aperture opening 41a, two slits 41b, two rotation pin holes 41c and two fixed pin holes 41d, in the same way as the substrates 33A and 34A.

The third substrate 41 is disposed between the first substrate 33A and the second substrate 34A. The first aperture blade portion 42, the first spacer 44 and second spacer 45, and the first fixed pin 40 are provided between the first substrate 33A and the third substrate 41, as shown in FIG. 11. Further, the second aperture blade portion 43, the first spacer-receiving portion 46 and second spacer-receiving portion 47, and the second fixed pin 48 are provided between the third substrate 41 and the second substrate 34A.

Figure 12:
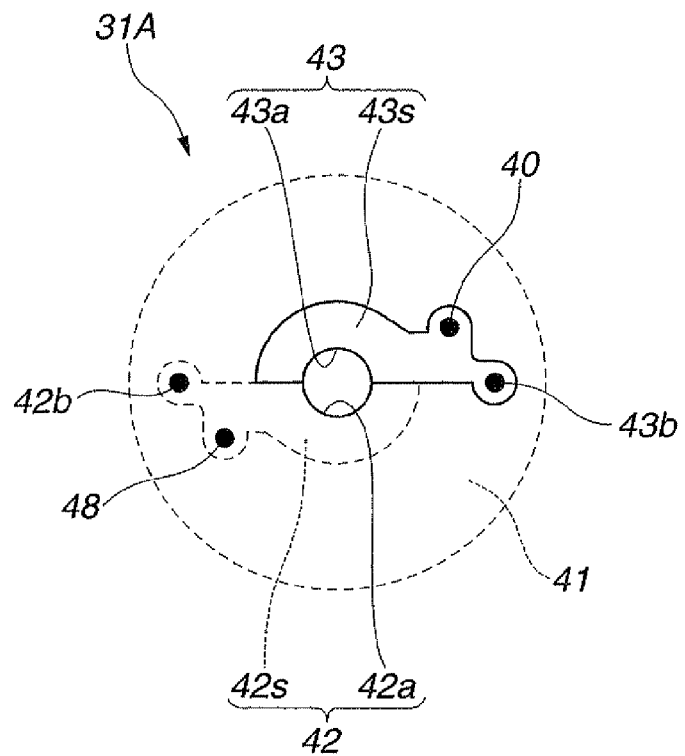
FIG. 12 is a diagram for explaining an aperture operation of the variable aperture mechanism and shows a state in which a pair of aperture blade portions is positioned over a fixed aperture opening.
Figure 13:
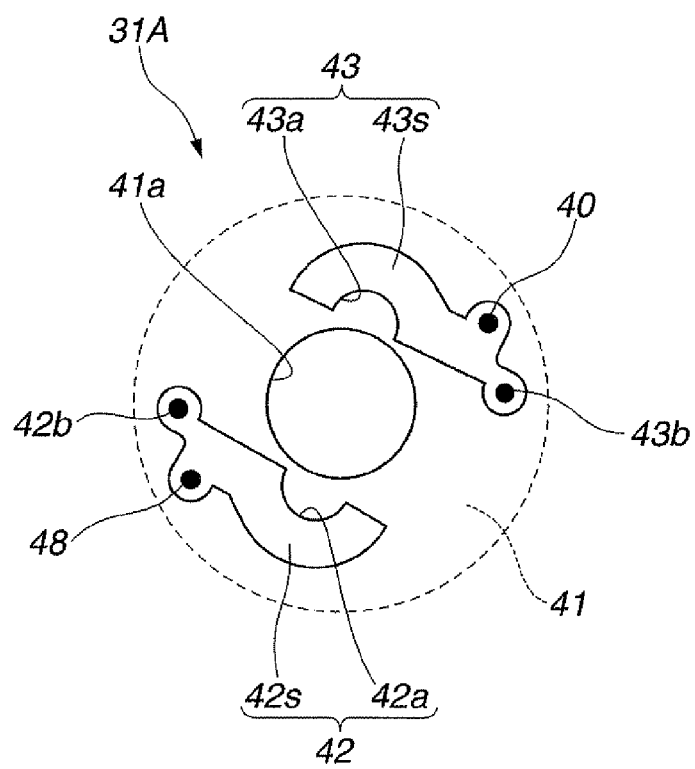
FIG. 13 is a diagram for describing an aperture operation of the variable aperture mechanism and shows a state in which the pair of aperture blade portions is positioned away from the fixed aperture opening.

The first aperture blade portion 42 and the second aperture blade portion 43 are configured with respective semi-circular aperture openings 42a and 43a formed in light-blocking portions 42s and 43s as shown in FIG. 11 to FIG. 13. The two aperture openings 42a and 43a form a minimum aperture opening diameter φ (see FIG. 2) when the first aperture blade portion 42 and the second aperture blade portion 43 have been moved into the state shown in FIG. 12. Note that an external diameter of a disc portion formed by the light-blocking portion 42s and the light-blocking portion 43s is larger than the external diameters of the fixed aperture openings 33a and 34a.

The first aperture blade portion 42 includes a rotation pin 42b and the second aperture blade portion 43 includes a rotation pin 43b. The rotation pin 43b of the second aperture blade portion 43 is cylindrical and projects from front and rear surfaces of the body. The rotation pin 43b may be integrated with the body of the second aperture blade portion 43 or provided as a separate entity. The rotation pin 43b is formed with a long projection length and projects towards the upper surface of the third substrate 41, which is downwards in FIG. 11. The rotation pin 42b of the first aperture blade portion 42, is formed with a long projection length, and points in the opposite direction to the rotation pin 43b of the second aperture blade portion 43, which is upwards in FIG. 11. In other words, the rotation pin 42b projects towards the lower surface of the third substrate 41.

The first aperture blade portion 42 includes a through hole 42c for passing the second driving pin 48, and the second aperture blade portion 43 includes a through hole 43c for passing the first driving pin 40.

The first spacer 44 and the second spacer 45 each includes a spacer body. Cylindrical fixed pins 44a and 45a are provided on a front surface side and a rear surface side of the spacer bodies. The fixed pins 44a and 45a may be integrated with the front and rear surfaces of the bodies or provided as separate entities to the bodies. After passing through the fixed pin holes 41d provided in the third substrate 41, the fixed pins 44a and 45a pass through the first and second spacer-receiving portion 46 and 47, and are located in the fixed pin holes 34d of the second substrate 34A.

The first driving pin 40 and the second driving pin 48 are cylindrical and may be integrated with the respective discs 40a and 48a or provided as separate entities. The first and second driving pins 40 and 48 project from the front and rear surfaces of the discs 40a and 48a. The first driving pin 40 projecting on the side of the first substrate 33A passes through the slit 33b of the first substrate 33A. Conversely, the first driving pin 40 projecting on the side of the third substrate 41 passes through the slit 41b in the third substrate 41, passes through the through hole 43c of the second aperture blade portion 43 and the slit 34b of the second substrate 34A, and then passes through the through hole 37a of the connecting portion 37 of the ion conducting actuator 36.

The second driving pin 48 projecting on the side of the second substrate 34A passes through the slit 34b in the second substrate 34A, and then passes through the through hole 37a of the connecting portion 37 of the ion conducting actuator 36. Conversely, the second driving pin 48 projecting on the side of the third substrate 41 passes through the slit 41b in the third substrate 41, passes through the through hole 42c of the first aperture blade portion 42, and then passes through the slit 33b of the first substrate 33A.

In this state, the rotation pin 42b projecting from the first aperture blade portion 42 on the side of the first substrate 33A is located in the rotation pin hole 33c of the first substrate 33A. Conversely, the rotation pin 42b projecting from first aperture blade portion 42 on the side of the third substrate 41 passes through the rotation pin hole 41c of the third substrate 41, and then is located in the rotation pin hole 34c of the second substrate 34A.

On the other hand, the rotation pin 43b projecting from the second aperture blade portion 43 on the side of the second substrate 34A is located in the rotation pin hole 34c of the second substrate 34A. Conversely, the rotation pin 43b projecting from the second aperture blade portion 43 on the side of the third substrate 41 passes through the rotation pin hole 41c of the third substrate 41, and then is located in the rotation pin hole 33c of the first substrate 33A.

In a procedure to assemble the variable aperture mechanism 31A of the above described configuration, a worker installs the first aperture blade portion 42, the spacers 44 and 45, and the first driving pin 40 in the stated order between the first substrate 33A and the third substrate 41.

The worker then installs the second aperture blade portion 43, the spacer-receiving portions 46 and 47, and the second driving pin 48 in the stated order between the third substrate 41 and the second substrate 34A. Next, the worker fits, in a similar manner to in the first embodiment, the first driving pin 40 and the second driving pin 48 protruding from the respective slits 34b in the second substrate 34A into the two through holes 37a of the connecting portions 37 included in the ion conducting actuator 36.

Thereafter, the worker electrically connects the signal lines 26a and 26b of the signal cable 26 to the front and rear surfaces of the ion conducting actuator 36 by soldering or the like, thereby completing the assembly of the variable aperture mechanism 31A of the second embodiment.

The following describes operations of the variable aperture mechanism 31A with reference to FIG. 12 and FIG. 13.

In the variable aperture unit 30 of the second embodiment, driving control of the variable aperture mechanism 31A is performed in substantially the same way as in the first embodiment. This is to say that the driving control is carried out according to operations by a surgeon on a switch of an operation portion, not shown of the endoscope. Based on an operation signal outputted from the switch, a driving control circuit located in the video processor is controlled to change a current of the driving signal.

For instance, the surgeon may perform an operation on the switch of the operation portion not shown, causing the operation portion to output a driving signal which causes an operation to stop down the aperture of the variable aperture unit 30. The resulting driving signal flows to the ion conducting actuator 36 of variable aperture mechanism 31A via the signal lines 26a and 26b and a voltage is applied.

Consequently, with the applied voltage, the ion conducting actuator 36 undergoes a contractile deformation so that the two connecting portions 37 approach each other by moving inward along an arc in the same way as in the first embodiment, as shown in FIG. 10 for example.

Note that, in the ion conducting actuator 36, both of the connecting portions 37 move towards fixed aperture opening 34a. Consequently, the first driving pin 40 and the second driving pin 48 passing through the connecting portions 37 are moved towards the fixed aperture opening 34a in the slits 34b, 33b and 41b. As a result, the first aperture blade portion 42 pivots around the rotation pin 42b and the second aperture blade portion 43 pivots around the rotation pin 43b.

The aperture opening 42a of the first aperture blade portion 42 and the aperture opening 43a of the second aperture blade portion 43 are positioned, as shown in FIG. 12, in the fixed aperture opening 33a of the first substrate 33A, the fixed aperture opening 34a of the second substrate 34A, and the fixed aperture opening 41a of the third substrate 41. Consequently, the fixed aperture openings 34a and 33a are blocked by the light-blocking portions 42s and 43s, and the aperture opening diameter of the variable aperture mechanism 31A is in a state of being stopped down to a minimum size. In other words, the aperture diameter is stopped down to the aperture internal diameter φ shown in FIG. 2 by the first aperture blade portion 42 and the second aperture blade portion 43.

The surgeon may then perform an operation on the operation portion switch not shown to halt the output of the driving signal to the variable aperture unit 30. Consequently, the application of the voltage to the ion conducting actuator 36 is halted, causing both connecting portions 37 to move toward the external circumference of the first substrate 33A and the second substrate 34A as shown in FIG. 10. The deformation returns the contracted ion conducting actuator 36 to an original state.

Note that both connecting portions 37 of the ion conducting actuator 36 move towards the periphery of the substrates 33A, 34A and 41 in the deformation operation.

Thus, the first driving pin 40 and the second driving pin 48 passing through the connecting portion 37 move in the slits 34b, 33b, and 41b in an opposite direction to the movement at aperture reduction. As a result, the first aperture blade portion 42 pivots around the rotation pin 42b to a position away from the fixed aperture openings 34a, 33a and 41a of the substrates 33A, 34A and 41, and the second aperture blade portion 43 pivots around the rotation pin 43b to a position away from the fixed aperture openings 34a, 33a and 41a of the substrates 33A, 34A and 41, as shown in FIG. 13.

Thus, the fixed aperture openings 34a, 33a and 41a are fully opened to give a maximum aperture opening diameter.

Note that in the variable aperture mechanism 31A of the second embodiment 2, by adjusting the current of the driving signal or switching on and off the output of the driving signal using the driving control circuit not shown in drawings of the video processors it is possible to halt the rotation operation of the first and second aperture blade portions 42 and 43 at a position between the stopped down state as shown in FIG. 12 and the open state as shown in FIG. 13 of the aperture. Thereafter, the first and second aperture blade portions 42 and 43 can be driven in steps.

In other words, it is possible to change the opening diameter of the fixed aperture openings 33a, 34a and 41a of the substrates 33A, 34A and 41 by controlling the rotation of the first aperture blade portion 42 and the second aperture blade portion 43 using switching operations.

Hence, in the variable aperture unit 30 of the second embodiment, it is possible to gradually stop down and gradually open the fixed aperture openings 33a, 34a and 41a. Also, since the variable aperture mechanism 31 of the variable aperture unit 30 is configured to include two blades, which are the first aperture blade portion 42 and the second aperture blade portion 43, the driving force for forming the aperture opening diameter is large, and a stable operating performance can be ensured.

Moreover, the provision of the first aperture blade portion 42 and the second aperture blade portion 43 makes it possible to gradually adjust the diameter of the aperture opening to obtain a desired amount of light. Hence, it is possible to reduce the diameter of the fixed aperture openings 33a, 34a and 41a formed in the substrates 33A, 34A and 41, and consequently, to reduce the external diameter of the bifocal lens 19 and the objective lens and promote the miniaturization of the image pickup apparatus 1. The other advantages resemble those of the first embodiment.

Third Embodiment

An image pickup apparatus of a third embodiment of the present invention is described with reference to FIG. 14 to FIG. 17.

Note that in FIG. 14 to FIG. 17, configuration elements resembling those of the first embodiment are marked with the same reference symbols, and descriptions of these configuration elements have been emitted. Only configuration elements which differ from those of the first embodiment are described.

Some types of conventional image pickup apparatus include a zoom mechanism. When an ion conducting actuator is used as the zoom mechanism actuator included in the image pickup apparatus, a range of movement in a moving lens frame is small due to the small amount of displacement in the ion conducting actuator.

To solve this problem, the image pickup apparatus 1 of the third embodiment is configured to allow a large amount of displacement in the ion conducting actuator.

Figure 14:
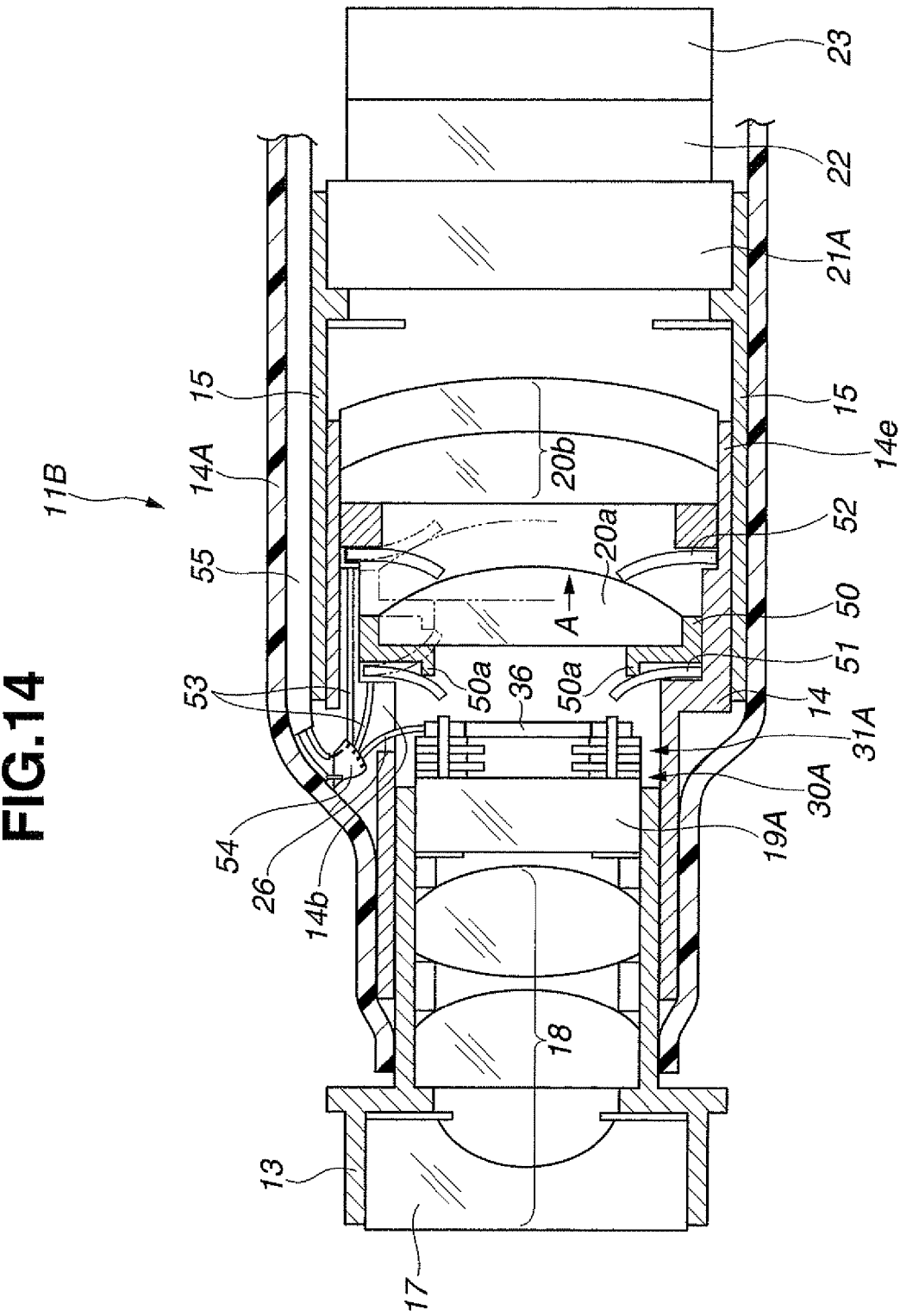
FIG. 14 is a cross-sectional view showing an image pickup apparatus of a third embodiment of the present invention for describing a configuration at the distal end side of an endoscope insertion portion equipped with the image pickup apparatus which includes an ion conducting actuator for moving a moving lens frame.

Specifically, an image pickup unit 11B of the image pickup apparatus 1 is configured to include, in the variable aperture unit 30A, the variable aperture mechanism 31A of the second embodiment, a first ion conducting actuator 51, a second ion conducting actuator 52, and a moving lens frame 50 holding an objective lens 20a, as shown in FIG. 14.

In other words, the variable aperture unit 30 has the variable aperture mechanism 31A which includes the first aperture blade portion 42 and the second aperture blade portion 43. In the variable aperture mechanism 31A, however, an infra-red cutting filter 19A which is a flat-plate plane lens is fixed by the fixing portion 35 in place of the bifocal lens 19.

Further, two objective lenses 20b, both held by a fourth lens frame 15, may be disposed on the proximal end side of the objective lens 20a.

An external circumferential section of the first ion conducting actuator 51 is fixed to a third lens frame 14 at a proximal end side of the variable aperture unit 30A, as shown in FIG. 14. A fulcrum for the displacement of the first ion conducting actuator 51 is positioned outside the external diameter of the objective lens 20a held by the moving lens frame 50.

A protruding portion 50a for contacting deformation portions (see reference symbol 57 in FIG. 16) of the first ion conducting actuator 51 is formed on the distal end side of the moving lens frame 50.

An external circumferential section of the second ion conducting actuator 52, on the other hand, is fixed to an extension portion 14e of the third lens frame 14 behind the moving lens frame 50 and in front of the objective lenses 20b as shown in FIG. 14. A fulcrum for displacement of the second ion conducting actuator 52 is positioned outside the external diameter of the objective lens 20a held by the moving lens frame 50. Note that the extension portion 14e of the third lens frame 14 serves to strengthen a fixing state of the second ion conducting actuator 52.

Figure 16:
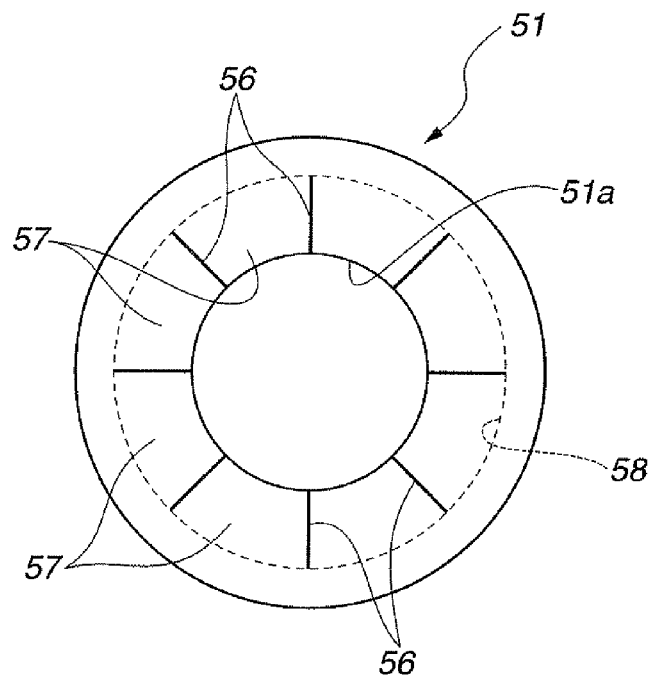
FIG. 16 is a plan view for describing a configuration of the ion conducting actuator.

The ion conducting actuators 51 and 52 have similar ring-form plate configurations, and the first ion conducting actuator 51 includes, for instance, an opening 51a and a plurality of deformation portions 57 as shown in FIG. 16. The plurality of deformation portions 57 is configured to include a plurality of radial cuts 56 on lines extending from the central axis of the opening 51a towards external circumference. A circular portion indicated by the broken line tying ends of the plurality of cuts 56 is a displacement line 58 indicating a deformation start line where the deformation of the plurality of deformation portions 57 begins and the inner peripheral portion is an active portion. When driven, the deformation portions 57 of the first ion conducting actuator 51 and the deformation portions 57 of the second ion conducting actuator 52 are displaced towards the distal end portion or the proximal end portion of the image pickup unit 11B. Note that a description of the configuration of the second ion conducting actuator 52 which has the same configuration as the first ion conducting actuator 51 is omitted.

Figure 15:
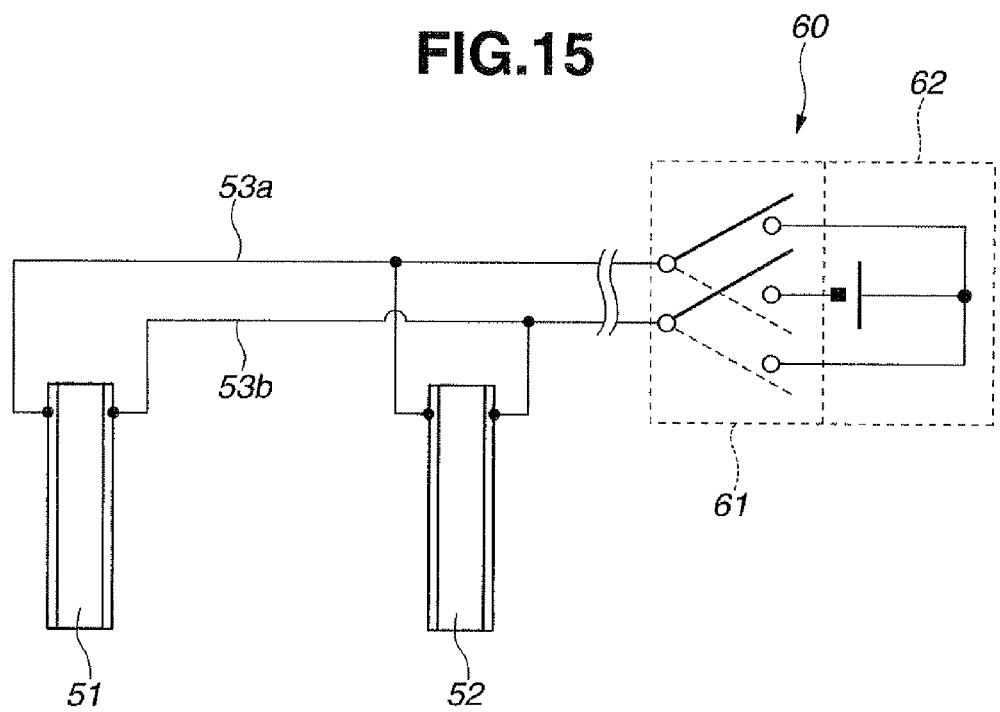
FIG. 15 is a block diagram for describing a configuration of an electrical circuit for driving the ion conducting actuator.

The ion conducting actuators 51 and 52 shown in FIG. 14 and FIG. 15 are connected by respective two signal lines 53a and 53b. The signal lines 53a and 53b are electrically connected to a cable connection substrate 54 via a through hole 14b in the third lens frame 14. The signal line 26 of the variable aperture unit 30A is electrically connected to the cable connection substrate 54.

A signal line 55 is connected to a proximal end of the cable connection substrate 54. The signal line 55 passes into the image pickup unit 11B and then through the signal cable 27.

The ion conducting actuators 51 and 52 of FIG. 15 are connected in parallel via the signal lines 53a and 53b to a driving controller 60 in the video processor, as shown in the circuit configuration for driving the ion conducting actuators 51 and 52 of FIG. 15.

The driving controller 60 includes a power source 62. The power source 62 is, for example, electrically connected to a switch 61 provided in the operation portion. The switch 61 includes two system output terminals which are connected to the signal lines 53a and 53b respectively.

According to the above-described configuration, the polarity of the driving signal flowing in the first ion conducting actuator 51 and the second ion conducting actuator 52 can be reversed by a switching operation on the switch 61.

Hence it is possible to displace the deformation portions 57 of the first ion conducting actuator 51 and the deformation portions 57 of the second ion conducting actuator 52 towards the distal end or the proximal end of the image pickup unit 11B using the switch operation. It is possible to increase the amount of the displacement over the conventional amount, even when an ion conducting actuator having conventional characteristics is used.

The first ion conducting actuator 51 and the second ion conducting actuator 52 are connected in parallel via the cable connection substrate 54 so a potential of the same polarity is applied to both by the power source 62. Hence, it is possible to drive the first and second ion conducting actuators 51 and 52 in the manner described above simply by connecting the two signal lines 53a and 53b. As a result, it is possible to reduce the amount of space used by the signal lines and thereby contribute to the miniaturization of the image pickup unit 11B.

The following describes operations of the image pickup apparatus of the above-described configuration with reference to FIG. 14.

In the endoscope image pickup unit 11B shown in FIG. 14, let an initial state be a state in which the objective lens 20a in the moving lens frame 50 is positioned farthest from the objective lens 20b on the proximal end side. In the image pickup unit 11B, the initial state corresponds to a tele-end position.

In the initial state, a voltage is applied to the ion conducting actuators 51 and 52 by supplying a driving signal based on operations on the switch 61 of the operation portion.

Due to the deformation property, the respective deformation portions 57 of the ion conducting actuators 51 and 52 deform towards the distal end of the image pickup unit 11B as shown by the solid line in FIG. 14.

At this point, the inner circumferential portion of the deformation portions 57 of the second ion conducting actuator 52 contacts a peripheral surface of the objective lens 20a in the moving lens frame 50, causing the moving lens frame 50 to move towards the distal end of the image pickup unit 11B. In other words, the moving lens frame 50 is disposed in the tele-end position by a pressing force from the deformation portions 57 of the second ion conducting actuator 52.

Next, suppose that the surgeon operates the switch 61 of the operation portion to perform a zooming operation. When the polarity of the driving signal supplied to the ion conducting actuators 51 and 52 is reversed, the respective deformation portions 57 of the ion conducting actuators 51 and 52 deform towards the proximal end of the image pickup unit 11B as shown by the broken line shown in FIG. 14.

Consequently, the inner circumferential portion of the deformation portions 57 of the first ion conducting actuator 51 contacts the protruding portion 50a of the moving lens frame 50, causing the moving lens frame 50 to move towards the proximal end of the image pickup unit 11B. In other words, the moving lens frame 50 is disposed in a wide-end position by a pressing force from the deformation portions 57 of the first ion conducting actuator 51.

When the image pickup apparatus 1 of the present embodiment uses ion conducting actuators with conventional characteristics as the first ion conducting actuator 51 and the second ion conducting actuator 52, the amount of displacement is larger than in a conventional image pickup apparatus. Consequently, the range of movement of the moving lens frame 50, which is to say the distance between tele-end position and the wide-end position, is larger than a conventional range of movement, and it is possible to improve the zooming performance.

Further, in the embodiment, it is possible to halt the supply of the driving signal to the ion conducting actuators 51 and 52 using a convenient operation on the switch 61. Hence, with an appropriate operation on the switch 61, the surgeon can halt the supply of the driving signal, and freely position the moving lens frame 50 between the tele-end position and the wide-end position.

Moreover, in the present embodiment, the driving control of the ion conducting actuators 51 and 52 works together with the variable aperture control of the variable aperture unit 30A. Thus, when a zooming mechanism using an ion conducting actuator is included, it is possible both to increase the amount of displacement of the ion conducting actuator over the conventional amount and obtain the same advantages as the first embodiment to increase the moving range of the moving lens frame. Hence, an advantage is obtained in terms of being able to improve the zooming performance.

Figure 17:
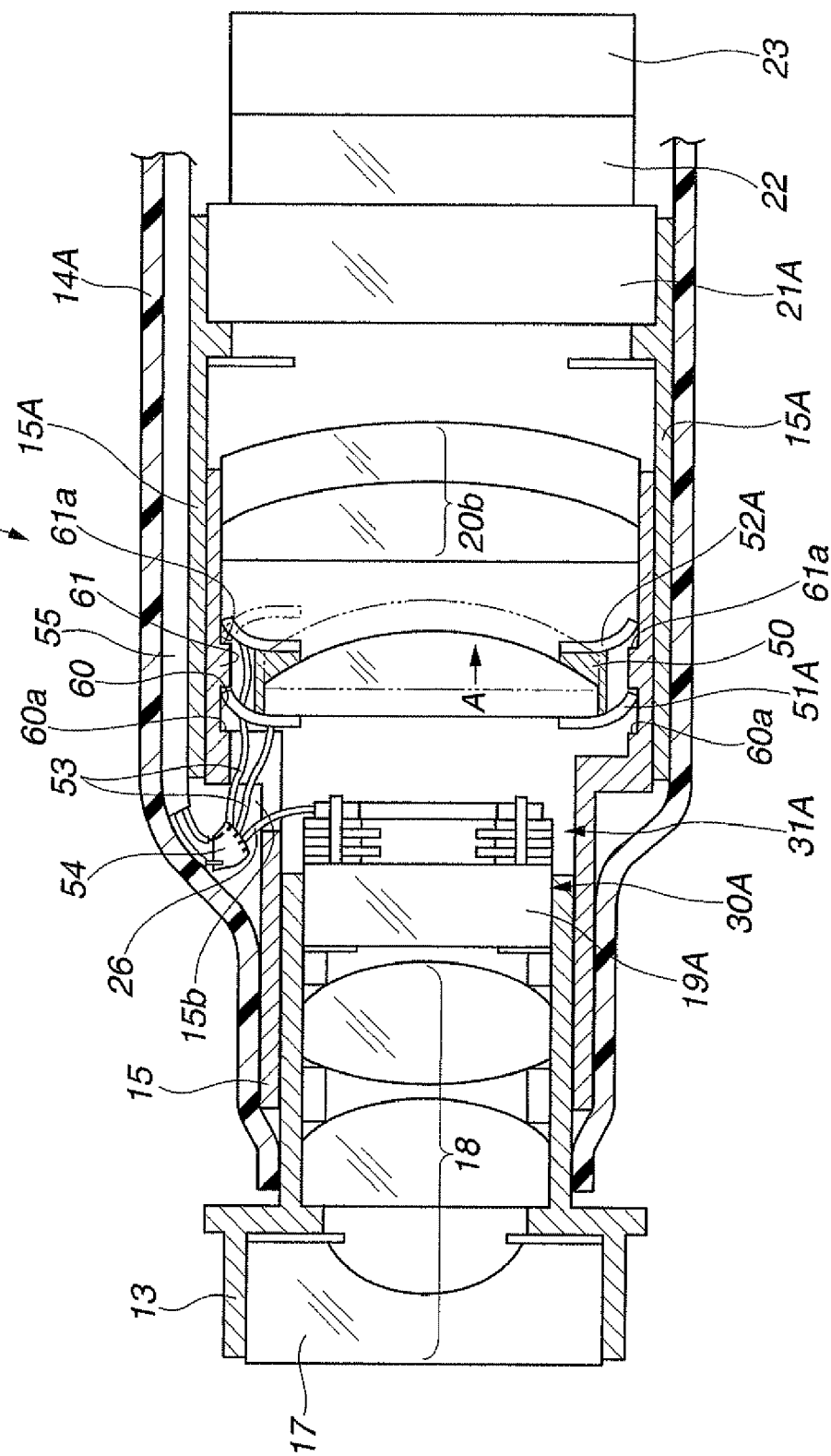
FIG. 17 is a cross-sectional view for describing a configuration of a distal end side of an endoscope insertion portion equipped with the image pickup apparatus including an ion conducting actuator which is a modification of the third embodiment.
Figure 18:
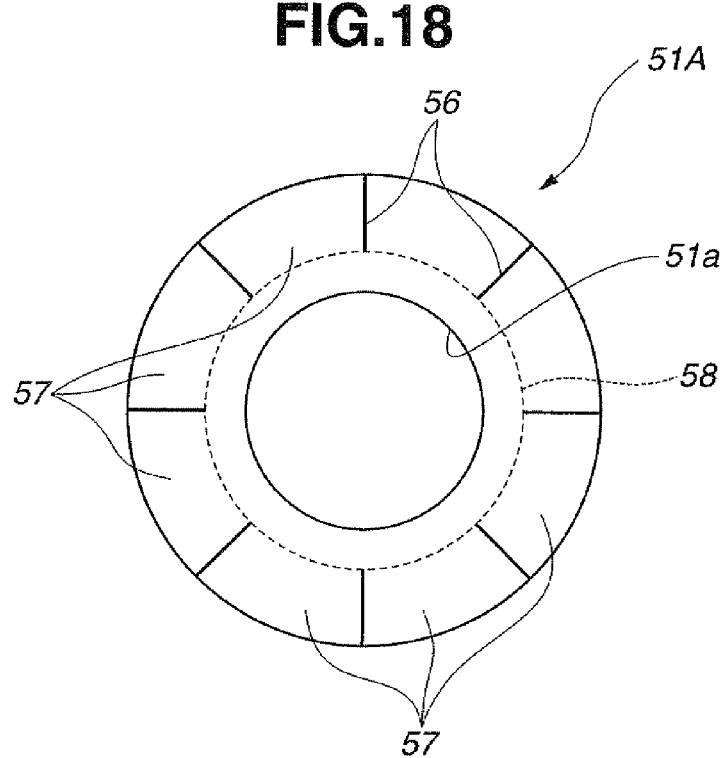
FIG. 18 is plan view for describing a configuration of the ion conducting actuator shown in FIG. 17.
Figure 19:
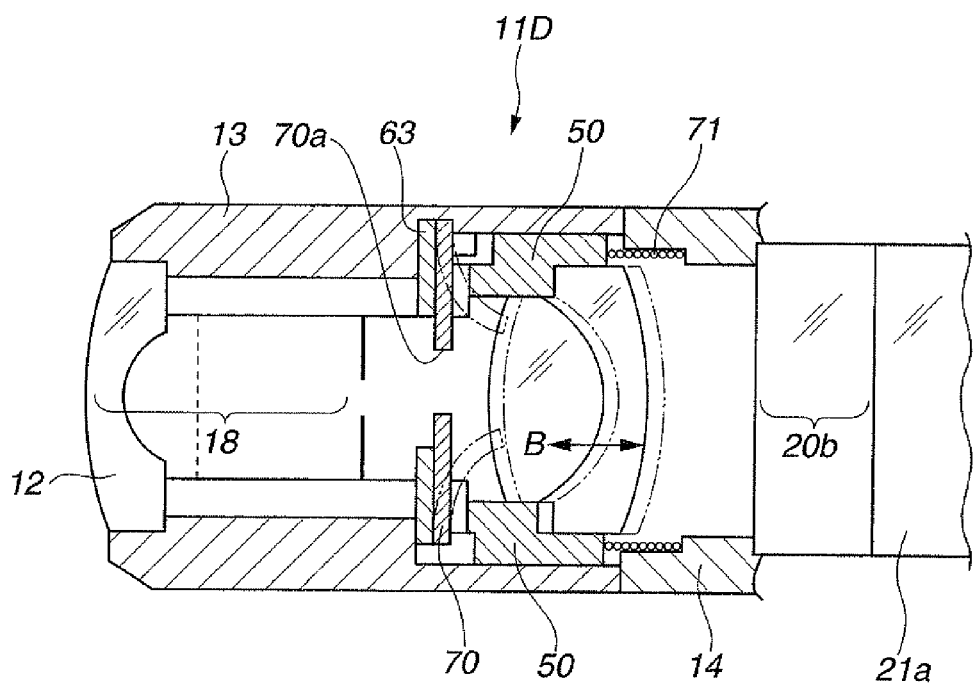
FIG. 19 is a cross-sectional view for describing a configuration of main parts of an image pickup apparatus which is a modification of the third embodiment and includes an ion conducting actuator which combines an aperture function.
Figure 20:
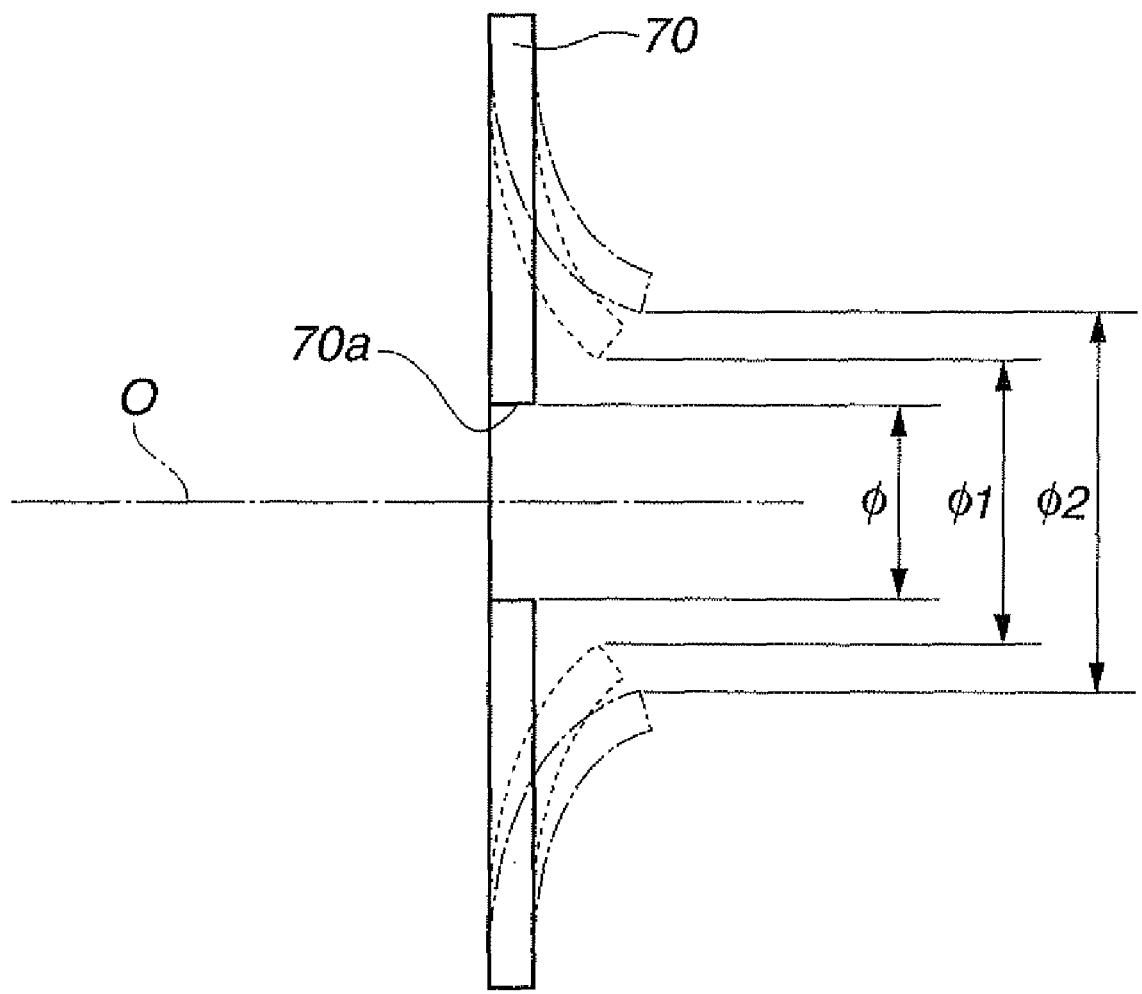
FIG. 20 is diagram for describing operations of the ion conducting actuator shown in FIG. 19.

Note that the ion conducting actuators of the third embodiment may be configured as shown in FIG. 17 and FIG. 18 or as shown in FIG. 19 and FIG. 20.

Modifications

A first modification to the ion conducting actuator is described with reference to FIG. 17 and FIG. 18. Note that in FIG. 17 and FIG. 18, configuration elements similar to those of the third embodiment are marked with the same reference symbols, and descriptions of these configuration elements have been omitted. Only configuration elements which differ from those of the third embodiment are described.

In the third embodiment, the moving lens frame 50 is moved by fixing the ion conducting actuators 51 and 52 to the third lens frame 14 and causing deformation in the plurality of deformation portions 57. In an image pickup unit 11C, however, the moving lens frame 50 is moved by fixing the first ion conducting actuator 51A and the second ion conducting actuator 52A to the moving lens frame 50 and the objective lens 20a, as shown in FIG. 17.

With this configuration, the first ion conducting actuator 51 having an opening 51a includes a plurality of radial cuts 56 extending from the external circumference side towards a center of the opening 51a, as shown in FIG. 18. Consequently, in the present example, the displacement line 58 is formed on the side of the opening 51a as shown by the broken line, and an external circumferential portion is an active portion. Note that a configuration of the second ion conducting actuator 52A resembles the configuration of the first ion conducting actuator 51A, and a description of the second ion conducting actuator 52A is therefore omitted.

According to this configuration, the plurality of deformation portions 57 are formed with the displacement line 58 as a deformation start line. The deformation portions 57 of the ion conducting actuators 51 and 52 displace toward the distal end or towards the proximal end of the image pickup unit 11C.

Specifically, the first ion conducting actuator 51A is fixed to a distal end side of the moving lens frame 50 and an incident surface side of the objective lens 20a at a section near the opening 51a thereof, for example, by bonding, as shown in FIG. 17.

An engagement groove 60 and an engagement protrusion portion 61 are formed in the third lens frame 14. The engagement groove 60 is provided so as to correspond to a placement position of the deformation portions 57 of the first ion conducting actuator 51A. A contact surface 60a which contacts the external circumferential portion of the deformation portions 57 is formed in the engagement groove 60. Moreover, a contact surface 61b which contacts the external circumferential portion of the deformation portions 57 is formed on the engagement protrusion portion 61.

The external circumferential portion of the deformation portions 57 of the first ion conducting actuator 51A is allowed to contact a contact portion 60b of the engagement groove 60 and a contact portion 61b located in front of the engagement protrusion portion 61.

On the other hand, the second ion conducting actuator 52A is fixed to a proximal end surface of the moving lens frame 50a at a section near the opening 52a thereof by bonding, as shown in FIG. 17.

A proximal end side of the engagement protrusion portion 61 of the third lens frame 14 is provided so as to correspond to a placement position of the deformation portions 57 of the second ion conducting actuator 52A. The external circumferential portion of deformation portions 57 is allowed to contact the proximal end side of the contact portion 61b of the engagement protrusion portion 61.

Other elements of the configuration are the substantially the same as those of the third embodiment.

Hence, according to the configuration of the image pickup unit 11C, by changing a polarity of the driving signal to control the driving of the ion conducting actuators 51A and 52A in the same way as in the third embodiment, it is possible to cause deformation in the deformation portions 57 contacting the contact portion 60b and the deformation portions 57 contacting the contact portion 61b and move the moving lens frame 50.

Note that in the present embodiment, the openings 51a and 52a of the ion conducting actuators 51A and 52A are formed to have opening diameters which do not affect the light incident on the objective lens 20a of the moving lens frame 50.

Further Modification

A further modification of the ion conducting actuator is described with reference to FIG. 19 and FIG. 20. Note that in FIG. 19 and FIG. 20, configuration elements similar to those of the third embodiment are marked with the same reference symbols, and descriptions of these configuration elements have been omitted. Only portions which differ from those of the third embodiment are described.

In the image pickup apparatus 1 of the third embodiment, the variable aperture function and the zooming function are achieved using the variable aperture unit 30A and the ion conducting actuators 51 and 52 which form the zooming mechanism. In the image pickup unit 11D shown in FIG. 19 and FIG. 20, on the other hand, the variable aperture function and the zooming function are achieved using a single ion conducting actuator 70.

As shown in FIG. 19, the image pickup unit 11D of the present embodiment includes a fixed aperture 63 held by the first lens frame 13 and provided behind the first lens group 18. An external circumferential portion of the ion conducting actuator 70 with the aperture function that enables changes in an opening diameter by deformation is fixed to an emission surface side of the fixed aperture 63.

The ion conducting actuator 70 with the aperture function includes an opening 70a which forms an aperture opening. The opening diameter of the opening 70a can be deformably changed among a minimum opening diameter $\phi$, an opening diameter $\phi1$ which is larger than the opening diameter $\phi$, and an maximum opening diameter $\phi2$ which is larger than the opening diameter $\phi1$, as shown in FIG. 20. Further, the ion conducting actuator 70 with the aperture function is arranged so that the opening diameter changes in the manner described above according to changes in a current value corresponding to the current value of a supplied driving signal.

To enable changes to the opening diameter, the ion conducting actuator 70 with the aperture function may include, for example, three cuts not shown in the drawing along lines extending from a central axis of the opening 70a towards the external circumference. Forming the three cuts gives the ion conducting actuator 70 a variable aperture deformation portion having an inner circumferential portion as an active portion. Consequently, it is possible to realize the ion conducting actuator 70 with the aperture function which allows the aperture opening diameter to be changed as shown in FIG. 20.

As shown in FIG. 19, a moving lens frame 50 is provided in the image pickup unit 11D. The objective lens 20a is held in the moving lens frame 50 so as to be in contact with the active portion of the variable aperture deformation portion when the ion conducting actuator 70 with the aperture function is driven.

According to this configuration, the moving lens frame 50 can be moved in a direction indicated by the arrow B of FIG. 19 by pressing forces of the variable aperture deformation portion resulting from the deformation of the variable aperture deformation portion when the ion conducting actuator 70 with the aperture function is driven. Note that symbol 71 denotes a spring. The spring 71 is provided in a distal end section of the third lens frame 14 on the proximal end side of the moving lens frame 50. The moving lens frame 50 is arranged so that an urging force from the spring 71 can move the moving lens frame 50 to the tele-end position of the image pickup unit 11D.

Hence, to return the moving lens frame 50 to the tele-end position, the driving of the ion conducting actuator 70 with the aperture function is halted. When the driving is halted, the moving lens frame 50 is moved towards the distal portion of the image pickup unit 11D and positioned at the tele-end position by the urging force of the spring 71 provided in the distal end section of the third lens frame 14 on the proximal end side of the moving lens frame 50.

Thus, with the image pickup unit 11D, it is possible to realize an image pickup apparatus 1 having both a variable aperture function and a zooming function using only the ion conducting actuator 70 with the aperture function, without providing the variable aperture unit 30 and a complex zooming mechanism. The above-described arrangement therefore contributes greatly to reductions in the size and of cost of the image pickup apparatus 1.

Note that the present invention is not limited to the above-described embodiments and various other modifications are possible without departing from the scope of the present invention.

What is claimed is:

1. An image pickup apparatus comprising a variable aperture unit, the variable aperture unit comprising;
    a bifocal lens for image pickup;
    a variable aperture mechanism including an aperture blade member operable to vary an aperture opening diameter of the bifocal lens, and a substrate for positioning the aperture blade member with respect to the bifocal lens and rotatably installing the aperture blade member in a direction orthogonal to a central axis of an opening diameter of the aperture; and
    a connecting portion for connecting and fixing a surface of the bifocal lens and the substrate of the variable aperture mechanism;
    wherein the bifocal lens is connected and fixed to the substrate of the variable aperture mechanism by the connecting portion in a state of being positioned to cause an optical axis of the bifocal lens to match a central axis of the aperture opening diameter when the aperture opening diameter is restricted by the aperture blade member of the variable aperture mechanism.

2. The variable aperture unit of the image pickup apparatus according to claim 1, wherein the substrate of the variable aperture mechanism includes:
    a pin hole for pivotally supporting a rotation pin of the aperture blade member; and
    a slit for slidingly move a driving pin of the aperture blade member for rotating the aperture blade member in a direction orthogonal to the central axis.

3. The image pickup apparatus according to claim 1, wherein the variable aperture mechanism includes an ion conducting actuator operable to vary the aperture opening diameter.

4. The image pickup apparatus according to claim 3, wherein the variable aperture mechanism includes an aperture blade member operable to be rotated by the ion conducting actuator and having an aperture opening.

5. The image pickup apparatus according to claim 3, wherein the variable aperture mechanism includes a pair of aperture blade members each operable to be rotated by the ion conducting actuator and having a semi-circular aperture opening.

6. An image pickup apparatus comprising:
    a lens unit including a plurality of lenses and a moving lens frame holding at least one of the plurality of lenses so as to allow movement of the at least one lens in an optical axis direction; and
    a zooming mechanism including an ion conducting actuator operable to move the moving lens frame provided in the lens unit;
    wherein the ion conducting actuator is a ring-like plate body and has a property of deforming according to a current passed through signal cables electrically connected respectively to front and rear surfaces of the plate body and the moving lens frame moves in the optical axis direction as a result of the deformation caused by passing the current.

7. An image pickup apparatus comprising:
    a lens unit including a plurality of lenses and a moving lens frame holding at least one of the plurality of lenses so as to allow movement of the at least one lens in an optical axis direction; and
    a zooming mechanism including an ion conducting actuator operable to move the moving lens frame provided in the lens unit;
    wherein the lens unit includes a first ion conducting actuator disposed in front of the moving lens frame and operable to move the moving lens frame towards a lens unit proximal end side and a second ion conducting actuator disposed behind the moving lens frame and operable to move the move lens frame towards a lens unit distal end side.

8. The image pickup apparatus according to claim 7 further comprising:
    a switch operable to reverse a polarity of a driving current flowing in the first ion conducting actuator and the second ion conducting actuator, wherein
    the first ion conducting actuator and the second ion conducting actuator move the moving lens frame towards one of the proximal end side and the distal end side based on switching of the polarity of the driving current flowing in the respective ion conducting actuators by the switch.

9. The image pickup apparatus according to claim 8, wherein
the first ion conducting actuator and the second ion conducting actuator are ring-form plate bodies having central opening portions, and
a section near the opening portions of the each ion conducting actuators is fixed to one of the moving lens frame and the lens held in the moving lens frame.

10. The image pickup apparatus according to claim 8, wherein
the first ion conducting actuator and the second ion conducting actuator are ring-like plate bodies having central opening portions, and
an external circumferential portion of each ion conducting actuator is fixed to a lens frame which movably holds the moving lens frame.

11. The image pickup apparatus according to claim 10, wherein fulcrums of the first ion conducting actuator and the second ion conducting actuator are positioned outside an external diameter of the lens held in the moving lens frame.

12. An image pickup apparatus comprising:
a lens unit including a plurality of lenses including a bifocal lens for image pickup and a moving lens frame for rendering one of the plurality of lenses moveable in an optical axis direction;
a variable aperture unit including: a variable aperture mechanism including an aperture blade member operable to vary an aperture opening diameter of the bifocal lens and rotated by an ion conducting actuator and a substrate for positioning the aperture blade member with respect to the bifocal lens and rotatably installing the aperture blade member in a direction orthogonal to a central axis of an opening diameter of the aperture; and a connecting portion for connecting and fixing a surface of the bifocal lens and the substrate of the variable aperture mechanism; and
a zoom mechanism including the ion conducting actuator which is a ring-like plate body and has a property of deforming so as to move the moving lens frame in the optical axis direction according to a current passed through signal cables electrically connected respectively to front and rear surfaces of the plate body.

13. An image pickup apparatus comprising:
a moving lens frame provided in a lens unit having a plurality of lenses, and operable to hold at least one of the plurality of lens so that the at least one lens is movable in an optical axis direction; and
a zoom mechanism provided in the lens unit and including an ion conducting actuator operable to move the moving lens frame, wherein
the ion conducting actuator includes, at a center thereof, an opening portion for varying an aperture opening diameter of the lens, and
the moving lens frame is moved in the optical axis direction according to changes in a variable state of the opening portion.

14. The image pickup apparatus according to claim 13, wherein
the ion conducting actuator has a property of deforming according to a current passed via an electrically connected signal cable, and
an opening diameter of the opening portion is varied according to the deformation caused by the passing of the current.

* * * * *